United States Patent [19]

Mikhail et al.

[11] Patent Number: 5,707,357
[45] Date of Patent: *Jan. 13, 1998

[54] BALLOON CATHETER HAVING PALPITATABLE DISCHARGE VALVE AND RETENTION COLLAR

[75] Inventors: Adel A. Mikhail, Bloomington; Gene E. Stobbs; Adel M. Hashw, both of Brooklyn Park; Shelley N. Johnson, Minnetonka, all of Minn.

[73] Assignee: C V Dynamics, Inc., Inver Grove Heights, Minn

[*] Notice: The term of this patent shall not extend beyond the expiration date of Pat. No. 5,624,395..

[21] Appl. No.: 605,435

[22] Filed: Feb. 22, 1996

Related U.S. Application Data

[63] Continuation-in-part of Ser. No. 546,572, Oct. 20, 1995, and Ser. No. 392,529, Feb. 23, 1995, abandoned.

[51] Int. Cl.⁶ .................................................. A61M 25/00
[52] U.S. Cl. ................................................................ 604/96
[58] Field of Search ................................ 604/93, 96, 104, 604/174, 256, 250, 247, 239, 329, 54, 55; 600/29-31; 128/DIG. 25; 251/342; 137/849

[56] References Cited

U.S. PATENT DOCUMENTS

| | | |
|---|---|---|
| 274,447 | 3/1883 | Kennish . |
| 3,331,371 | 7/1967 | Rocchi et al. . |
| 3,438,375 | 4/1969 | Ericson . |
| 3,459,175 | 8/1969 | Miller . |
| 3,503,400 | 3/1970 | Osthagen et al. . |
| 3,731,670 | 5/1973 | Loe . |
| 3,756,243 | 9/1973 | Schulte . |
| 3,758,073 | 9/1973 | Schulte . |
| 3,768,102 | 10/1973 | Kwan-Lett et al. . |
| 3,812,841 | 5/1974 | Isaacson . |
| 3,841,304 | 10/1974 | Jones . |
| 3,865,666 | 2/1975 | Shoney . |
| 3,924,634 | 12/1975 | Taylor et al. . |
| 3,959,429 | 5/1976 | Beuning . |
| 3,967,645 | 7/1976 | Gregory . |
| 3,977,408 | 8/1976 | Mackew . |
| 3,985,601 | 10/1976 | Panagrossi . |
| 4,026,298 | 5/1977 | Grausz . |
| 4,089,337 | 5/1978 | Kronner . |
| 4,188,954 | 2/1980 | Patel et al. . |
| 4,210,478 | 7/1980 | Shoney . |
| 4,222,384 | 9/1980 | Birwell . |
| 4,225,371 | 9/1980 | Taylor et al. . |
| 4,284,459 | 8/1981 | Patel . |
| 4,335,723 | 6/1982 | Patel . |
| 4,432,757 | 2/1984 | Davis, Jr. . |
| 4,457,299 | 7/1984 | Cornwell . |
| 4,553,959 | 11/1985 | Hickey et al. . |
| 4,587,954 | 5/1986 | Haber . |
| 4,643,169 | 2/1987 | Koss et al. . |
| 4,710,169 | 12/1987 | Christopher . |
| 4,813,935 | 3/1989 | Haber et al. . |
| 4,822,333 | 4/1989 | Lavarenne . |
| 4,846,784 | 7/1989 | Haber . |
| 4,932,938 | 6/1990 | Goldberg et al. . |
| 4,946,449 | 8/1990 | Davis, Jr. . |
| 4,968,294 | 11/1990 | Salama . |
| 5,030,199 | 7/1991 | Barwick et al. . |
| 5,041,092 | 8/1991 | Barwick . |
| 5,078,676 | 1/1992 | Railly . |

(List continued on next page.)

*Primary Examiner*—Manuel Mendez
*Attorney, Agent, or Firm*—Moore & Hansen

[57] ABSTRACT

An indwelling urinary catheter having a palpitatable multi-axial dome-type valve and an inflatable anchoring balloon. The valve has a peripheral trough to maximize drainage. The catheter body and balloon are integrally molded from silicone to produce a uniform and symmetrical balloon shape. The balloon shape may be selectively altered by varying bonding patterns or wall thicknesses. Valve openings traverse an arcuate pathway, and adjacent valve elements are separated by an intermediate rib to ensure a reliable closure. Valve elements are readily displaced by a drainage tube connector that engages the valve body. A collar on the catheter body moves axially along helical threads to adjust tension on the balloon.

33 Claims, 16 Drawing Sheets

U.S. PATENT DOCUMENTS

| | | |
|---|---|---|
| 5,090,424 | 2/1992 | Simon et al. . |
| 5,114,398 | 5/1992 | Trick et al. . |
| 5,131,906 | 7/1992 | Chen . |
| 5,224,938 | 7/1993 | Fenton, Jr. . |
| 5,226,890 | 7/1993 | Ianniruberto et al. . |
| 5,234,409 | 8/1993 | Goldberg . |
| 5,306,226 | 4/1994 | Salama . |
| 5,350,363 | 9/1994 | Goode et al. . |
| 5,360,402 | 11/1994 | Conway et al. . |
| 5,395,352 | 3/1995 | Penny . |
| 5,409,464 | 4/1995 | Villalobos . |

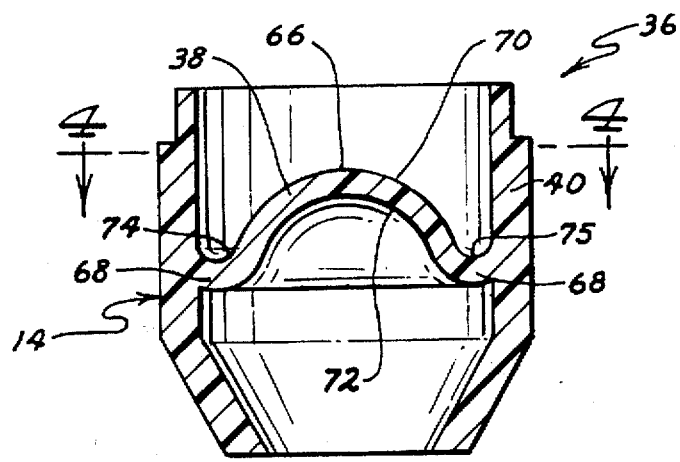
FIG. 3
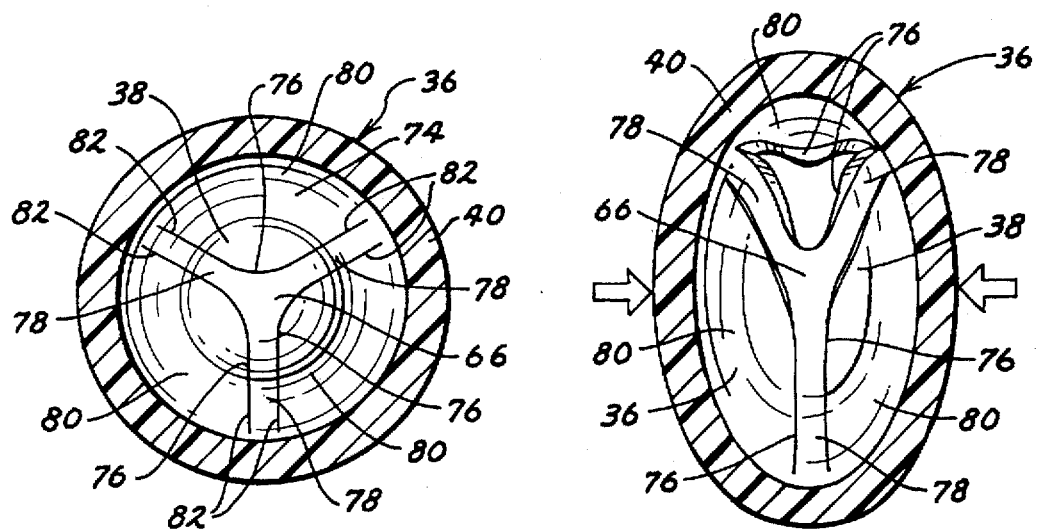
FIG. 4
FIG. 5

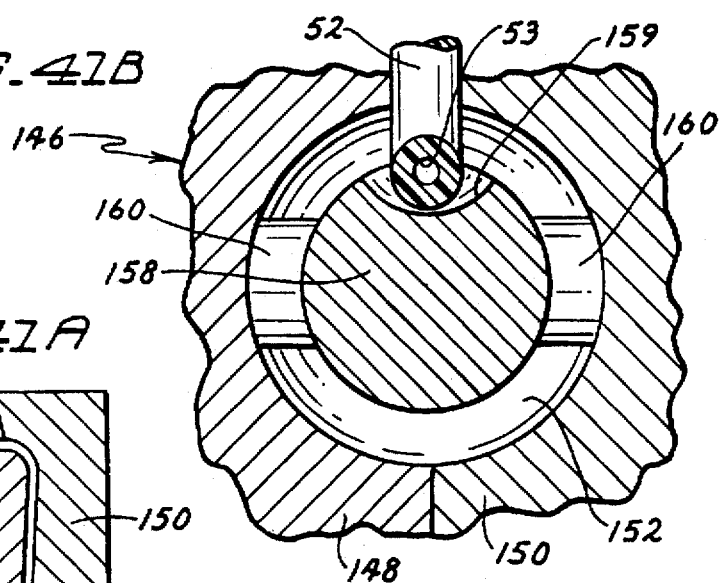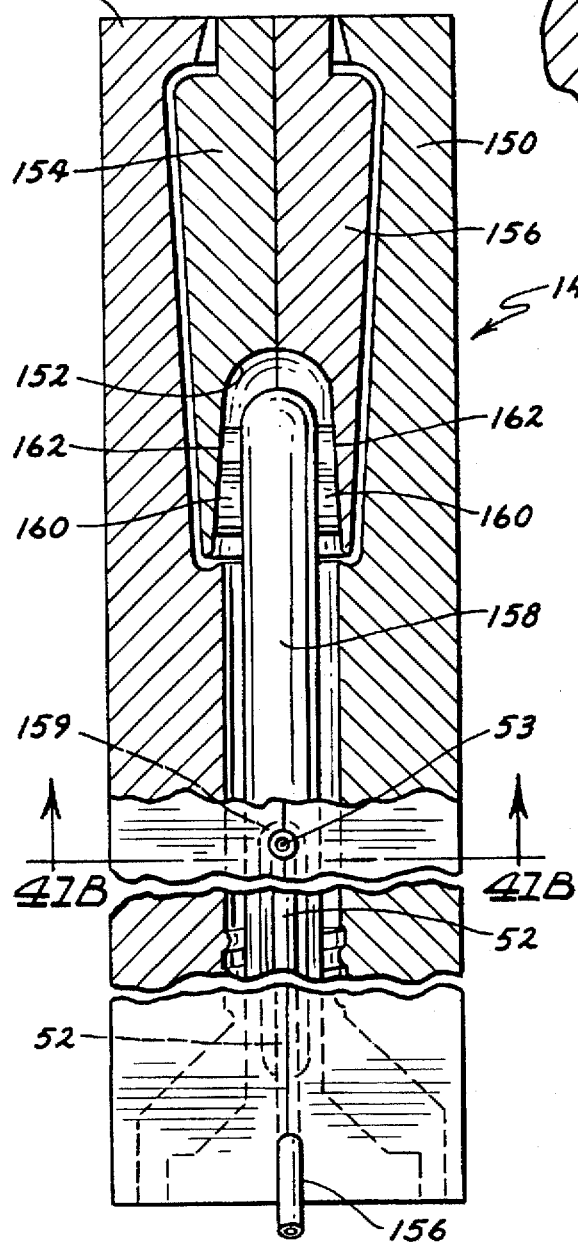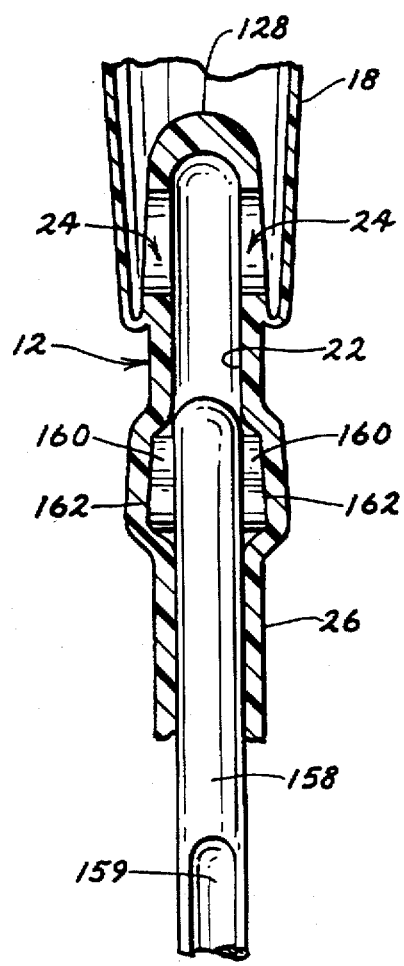

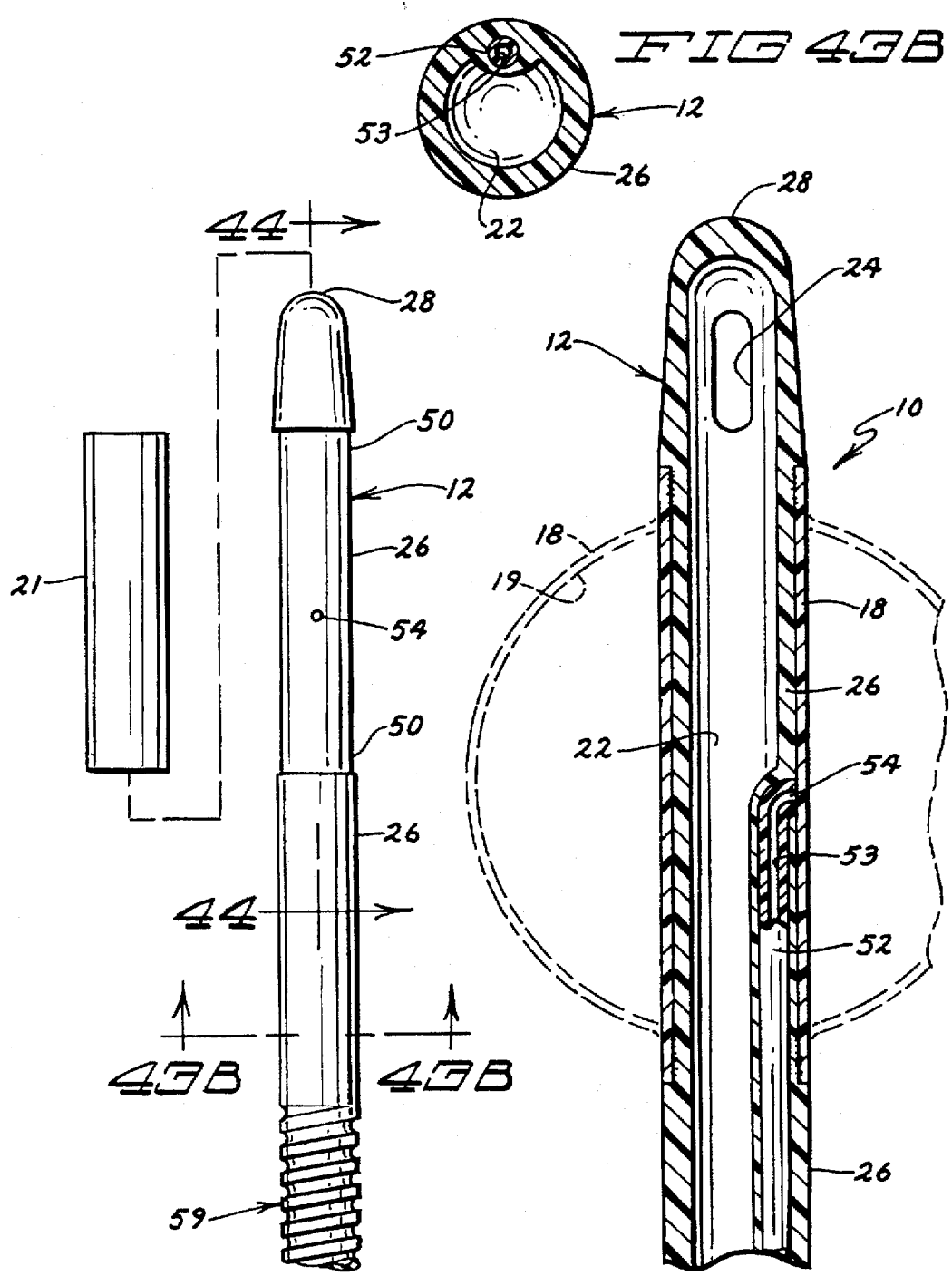

BALLOON CATHETER HAVING PALPITATABLE DISCHARGE VALVE AND RETENTION COLLAR

BACKGROUND OF THE INVENTION

This a continuation-in-part of application Ser. Nos. 08/392,529 filed on Feb. 23, 1995, and Ser. No. 08/546,572 filed on Oct. 20, 1995, each entitled URINARY CATHETER HAVING PALPITATABLE VALVE AND BALLOON AND METHOD FOR MAKING SAME, and for which the benefit of priority is hereby claimed pursuant to 35 USC §120. Each of the aforementioned applications is hereby incorporated herein by reference.

1. Field of Invention

This invention relates generally to balloon catheters for managing urinary incontinence and retention, and particularly intra-urethral or "indwelling" Foley-type urinary catheters having an externally located multiaxial palpitatable discharge valve and retention collar.

2. Prior Art

The field of urinary catheters has long been dominated by the Foley-type catheter, which is well known in the art and comprises an inflatable balloon for disposition within a patient's bladder and a discharge or drainage tube which extends from the bladder, through the urethra, to the exterior when the catheter is in place within the patient. The Foley-type catheter provides passive urinary drainage, and the ability to clamp the catheter closed at a location exterior of the patient. Representative examples of Foley-type catheters are shown in U.S. Pat. Nos. 4,055,187; 4,154,243; 4,188, 954; and 4,335,723 to Patel.

Foley-type catheters have many drawbacks. These drawbacks include, among other things, relatively high intra-urethral leakage rates, the inability to selectively control discharge, and the diminution in the patient's mobility or physical activities due to the constant need for a drainage collection device interconnected to the open catheter.

Many attempts have been directed towards solving these problems, and the prior art reflects that many basic improvements have been adopted and combined in a variety of forms to optimize the function of the particular catheters. However, practical, reliable, and commercially viable alternatives are still needed.

One alternative provides a releasable connection between the Foley-type catheter and the external drainage tube to enhance mobility, as shown in U.S. Pat. No. 4,955,858 to Drews. A check valve can also be disposed at a point along the catheter or drainage tube as shown in U.S. Pat. No. 3,967,645 to Gregory. However, these improvements do not address other problems such as an intra-urethral leakage, and have not resulted in a solution that is satisfactory for most patients.

The use of an inflatable balloon or other blocking device to minimize intra-urethral leakage around the exterior of the catheter, and valves disposed within the catheter body to permit selective voiding, are considered fundamental advances in the art. Early examples of developments along these lines include U.S. Pat. No. 3,841,304 to Jones and U.S. Pat. No. 3,503,400 to Osthagen. A blocking device comprising a hydrogel collar disposed around the catheter tube of a Foley-type catheter is disclosed. The collar is designed to slide axially along the catheter tube into contact with the body at the distal end of the urethra to hold the balloon in sealing contact with the neck and orifice of the bladder. The collar also provides an additional obstacle to leakage at the distal end of the urethra.

Valves contained within catheters that can be manipulated by bending, flexing, or extending the catheter are shown in U.S. Pat. No. 4,822,333 to Lavareene; and U.S. Pat. Nos. 4,432,757 and 4,350,161 to Davis. These catheters are generally unsuitable for use by female patients, and are subject to leakage resulting from normal body movement when used in male patients.

Collapsible- or restricted-lumen catheters that have predetermined release pressure thresholds have also been disclosed. However, these catheters are subject to leakage, do not drain completely, and have predetermined operational pressure ranges which may not be appropriate for a large number of patients without undue experimentation particularly when determining a safe high end limit to the range. In addition, the relatively short distance between the orifice of the bladder and the distal end of the urethra in female patients limits the suitability of some designs that require an extended length of lumen to maintain the requisite pressure threshold. Representative examples of such designs are shown in U.S. Pat. No. 4,553,959 to Hickey and U.S. Pat. No. 3,672,372 to Heimlich.

Other variations unique to male or female patients have also been disclosed. An exterior sheath is one example of a device suitable only for male patients, as shown in U.S. Pat. Nos. 5,334,175 and 5,176,666 to Conway; U.S. Pat. No. 4,710,169 to Christopher; and U.S. Pat. No. 4,626,250 to Schneider.

U.S. Pat. No. 5,234,409 to Goldberg; U.S. Pat. No. 5,114,398 to Trick; and U.S. Pat. No. 5,030,199 to Barwick show representative examples of valved catheters designed for female patients. These catheters incorporate a variety of valves and actuators which illustrate some of the inherent obstacles in designing catheters for female patients, namely providing a manipulable or palpitatable valve that can be located and gripped by the patient without presenting a hygienic risk or being inconvenient for the patient to operate.

Intra-urethral plug-type devices have also been disclosed. These devices include palpitatable or manually activated valves for selective control over voiding. They are generally retained within the distal end of the patient's urethra using inflatable bulbs, radial serrations, or regions of enlarged diameter, and generally include an exposed portion that permits selective activation of the valve or periodic removal of the device. Representative examples of such devices are shown in U.S. Pat. No. 5,131,906 to Chen; U.S. Pat. No. 5,090,424 to Simon; U.S. Pat. No. 4,968,294 to Salama; U.S. Pat. No. 4,457,299 to Cornwall; and U.S. Pat. No. 3,768,102 to Kwan-Gett.

A wide variety of discharge valve designs have been contemplated for use with urinary catheters. These valves are usually actuated mechanically, but may also be actuated magnetically or by other means. The more prevalent types of mechanical valves include ball-and-seat, duckbill, inflatable check, plug, and dome-type valves. These valves may all be operated manually by the patient, however, some types of valves are identified as "palpitatable" based upon a portion of the valve being squeezed or pressed in order to open the valve. The palpitatable valve may be disposed internally or externally for male patients, although internal valves may be more difficult to use, uncomfortable, and unreliable. The palpitatable valve must be located externally for a female patient. Palpitatable discharge valves may also be classified as orientation-dependent (uniaxial) or orientation-independent (multiaxial), based upon whether pressure must be applied to a pair of selected points or surfaces in order to open the valve sufficiently for normal discharge operation, or whether the valve will open when pressure is exerted radially from any two opposing directions.

These basic types of mechanical, inflatable, and palpitatable valve configurations are displayed in U.S. Pat. No. 5,306,226 to Salama; U.S. Pat. Nos. 5,269,770 and 5,261,896 to Conway; U.S. Pat. No. 4,946,449 to Davis; U.S. Pat. No. 4,932,938 to Goldberg; U.S. Pat. Nos. 4,846,784 and U.S. Pat. No. 4,813,935 to Haber; and U.S. Pat. No. 4,643,169 to Kross, as well as several other references previously discussed. Representative examples of magnetically-actuated valves are shown in U.S. Pat. No. 5,041,092 to Barwick and U.S. Pat. No. 4,731,670 to Loe.

The Davis '449, Goldberg '938, and Haber '794 patents disclose several types of palpitatable valves that may be disposed internally or externally. A uniaxial duckbill valve may be rotated between the user's fingers until pressure is directed on the proper sites to maximize fluid flow, but the rotational torque can cause irritation, inflammation, and leakage. The Goldberg '938 patent teaches a tactile sensing means for determining the proper orientation of a duckbill valve to ensure complete opening, however properly orienting the catheter and valve upon initial insertion still requires time and training. In addition, the Davis '449 and Goldberg '938 patents both disclose dome-type valves that operate substantially the same as uniaxial duckbill valves. These dome-type valves similarly provide two opposing valve elements, but the slit or cut forming the valve opening approaches or intersects the side wall of the valve at a point below or downstream of the apex of the dome. While this configuration provides enhanced drainage capabilities for small aliquots of fluid remaining within the valve body compared with conventional duckbill valves, the proximity of the ends of the slit to the side wall of the catheter body restricts the amount that the valve can be opened in the region nearest the side wall (and therefore the lowest or most downstream portion of the valve) and risks nicking or scoring the side wall of the valve when the slit is cut. One alternative shown in the Davis '449 patent appears as a separate dome-shaped valve piece that is cut and inserted within the catheter body, which does not eliminate the restriction on the width of the valve opening adjacent the side wall of the valve body, and requires additional time, labor, costs, and quality control measures to accommodate the additional manufacturing steps.

The Davis '449 patent further shows a drainage tube connector being inserted through the dome-type valve to hold the valve in an open position. Similarly, U.S. Pat. No. 3,421,509 to Fiore discloses a protective sleeve for a urinary catheter having several overlapping wedge-shaped flap elements that are opened by insertion of a drainage tube connector.

The Haber '784 patent discloses another valve design similar in longitudinal cross section to a duckbill valve, wherein the valve elements are lobes having extended contact surfaces that present a central lumen when pressure is applied, rather than conventional blade-type elements that pivot apart when the valve is deformed.

The use of duckbill valves having pivotal blade elements or dome-type valves having single or cross-shaped slits are generally preferred for palpitatable valves. However, existing catheter designs having palpitatable valves do not provide as reliable a closure under normal pressures as is generally desired. In addition, the valves do not adequately drain small aliquots of urine from within the valve, thereby fostering a highly infectious environment located in close proximity to contamination from the outside environment and a pathway for ready transmission of bacteria infection to the bladder.

The prior art patents also disclose several different balloon structures that are diagrammatically shown as generally spherical or toroidal in shape, and which seat against a substantial area surrounding the neck and orifice of the bladder. However, results using these types of balloon structures have not been highly successful. As previously noted, an unacceptable rate of leakages is still exhibited when using these balloons depending upon (1) the underlying combination of balloon and catheter designs, (2) the peculiarities of the particular patient's anatomy, (3) the uniformity in fabricating the specific balloon and catheter, and (4) the pliability or malleability of the inflated balloon. While one alternative is the use of solid, deformable, compressible, or elastic blocking members that are disposed at or within the neck of the bladder, balloon catheters are predominantly viewed as the superior choice due to their (1) relative ease of insertion and fixation, (2) minimization of patient discomfort, and (3) the decreased likelihood of tissue injury or damage compared with inserting more rigid structures through confined passages.

Solutions to the intra-urethral leakage problem associated with Foley-type balloon catheters have been proposed, usually involving seating the lower portion of the balloon within the neck and orifice of the bladder to form a plug-type seal. One method for accomplishing this is to use a balloon that can be deformed by pulling downwardly on the catheter tube or body to draw a portion of the balloon into the neck or orifice, such as disclosed in the Jones '304 patent. Another alternative is to inflate a portion of the balloon and catheter within the neck and orifice to form a plug-type seal. The Salama '226 patent describes a pear-shaped balloon that is inflated and the lower portion is seated within the neck and orifice of the bladder, and the Davis '938, '449, and '757 patents disclose inflating a tapered segment of the catheter wall between the balloon and a urethral cuff disposed proximate to the prostatic urethra. However, these types of designs are not believed to be particularly successful or desirable since the interior shape of the neck of the bladder varies both from patient to patient and between males and females, approaching shapes in some patients that are pyramidal rather than conical or tubular, thus preventing proper seating within the neck or orifice by a balloon having a circular radial cross section, and because inflating the balloon or catheter wall within the urethra exerts pressure that can lead to inflammation, infection, necrosis, or an unacceptable decline in tissue elasticity.

While these developments in urinary catheters have been proceeding, other ancillary improvements have also been made. For example, the Conway '770 and '896 patents disclose the use of bactericidal and microbicidal agents to prevent infection, as well as methods for sustained release of those agents from a polymeric matrix coating or through a permeable membrane surrounding the catheter wall. The Conway '379 and '671 patents teach various manufacturing methods for coated balloon catheters and lubricated sleeves for use with those catheters.

In view of the many shortcomings and patient dissatisfaction with existing designs for urinary catheters, Applicants have therefore developed a preferred urinary catheter design intended to meet the needs and desires of the majority of male and female patients suffering from incontinence or retention disorders.

Applicants have also determined that several shortcomings presented by the prior art urinary catheter systems were not caused by inherently defective designs, but a basic misapprehension among those skilled in the art regarding the manufacturing methods that should be employed to fabricate urinary catheters and balloons that are operable for their intended purpose and consistently reliable For example, urinary catheters and balloons are conventionally fabricated from latex or a synthetic polymer using a multi-step dipping and curing process to form and strip successive layers of material to produce a catheter and balloon. The balloon and catheter may be formed integrally or unitarily, or may be bonded together.

However, the lack of control over the dipping, curing, and bonding processes inherently produces catheter balloons that are irregular or nonuniform in shape when inflated, or which are asymmetrically disposed relative to the catheter body. This lack of sufficient uniformity and symmetry may result in intra-urethral leakage on the exterior of the catheter, whereas proper uniformity and symmetry can minimize leakage without the need for a plug-type seal within the urethra or neck of the bladder. Additional problems have been encountered with dipped catheters, such as delamination and blockages in the inflation lumen.

While dipping and curing latex catheters is the prevalent manufacturing method, it should be noted that various molding processes have been utilized in the past. U.S. Pat. Nos. 4,210,478 and 3,865,666 to Shoney and U.S. Pat. No. 3,959,429 to Benning disclose various methods and devices for molding a balloon onto an already-molded segment of a catheter body. The Shoney '666 patent further discloses an inverted or proximally-attached balloon that is later adhered or bonded to the catheter at its distal end. However, the processes described do not contemplate the unitary fabrication of the catheter body and balloon, thus requiring many additional manufacturing steps and subjecting the catheter body to multiple curing processes, both of which can have a detrimental effect on the uniformity and reliability of the catheter and balloon. U.S. Pat. No. 4,222,384 to Birtwell discloses molding a catheter tip and balloon as one piece to achieve an inverted balloon. However, the tip and balloon must be molded or adhered to an existing catheter body. In addition, the balloon must be folded or rolled during subsequent manufacturing steps, thus increasing the complexity of the manufacturing process and the likelihood of damage to or distortion of the catheter or balloon. In contrast, U.S. Pat. No. 4,225,371 to Taylor teaches molding the balloon to the catheter body, with the unattached end of the balloon being adhered or bonded to the tip of the catheter after it is subsequently attached. As in the case of the designs discussed above, multiple manufacturing and assembly steps are required to combine and attach the various components, thereby mitigating against automated assembly, increasing the time and labor necessary to fabricate each catheter, requiring additional testing and quality-control operations, and multiplying the opportunities for and likelihood of occurrences that will diminish the reliability, uniformity, or operability of the final product. Even where the catheter tip is molded together with another portion of the catheter, additional time-consuming fabrication steps are frequently necessary to complete the catheter, such as manually punching each of the "Murphy eyes" through the proximal tip of the catheter body, a process which requires placing the catheter on a fixture, punching the eyes, removing the catheter from the fixture, and verifying the punched material has been completely excised from the catheter body.

BRIEF SUMMARY OF THE INVENTION

It is therefore one object of this invention to design an indwelling urinary catheter system of the type having: (1) a catheter body disposed within the urethra of the patient for extended periods of time, (2) a palpitatable valve that may be selectively manipulated by the patient for voiding urine, and (3) an inflatable balloon disposed within the bladder to minimize intra-urethral leakage along the exterior of the catheter.

It is a related object of this invention to fabricate the above urinary catheter system using a process that optimizes the uniformity and reliability of the catheters.

It is a distinct object of this invention to fabricate the above urinary catheter system using a method that may be easily automated, in whole or in part, as desired to meet practical manufacturing and regulatory requirements.

It is another object of this invention to design the above urinary catheter system so as to incorporate a multiaxial palpitatable discharge valve which may be conveniently operated by male and female patients.

It is a related object of this invention to design the multiaxial valve such that it consistently provides a reliable closure at both low or high fluid pressures, drains completely at low or negligible fluid pressures, and permits the passage of a drainage tube connector for extended use by immobile or incapacitated patients.

It is an additional object of this invention to fabricate the above multiaxial valve using a method that enhances or enlarges the valve's seating or contact area compared with conventional duckbill or dome-type valves, and ensures that the valve elements consistently and reliably return to the proper closed configuration.

It is yet another object of this invention to design the urinary catheter system such that it may be readily adjusted to match the particular anatomical characteristics of a patient and will remain configured as adjusted, and in particular accommodates continuous incremental adjustments of the catheter length for female patients.

It is a further object of this invention to design the above urinary catheter such that the valve may be disposed externally of the patient, and wherein the exterior shape of the valve body reduces the potential for inadvertent or accidental deformation of the valve due to contact or pressure with the patient's clothing or legs, and further provides a rapid and secure connection for a drainage tube that maintains the valve in an open position.

It is yet another object of this invention to provide the above urinary catheter with the capability to adjust the pressure exerted on the inflatable balloon to a desired level to mitigate against dislodgement of the balloon from the neck and orifice of the bladder.

It is still another object of this invention to provide the above urinary catheter with a reservoir for the accumulation of an antiseptic gel to form a liquid seal against the egress of urine from the urethra, and a barrier against the ingress or migration of infectious contaminants, along the exterior of the catheter.

Briefly described, the urinary catheter system of this invention includes a catheter body disposed within the urethra of the patient for extended periods of time, a palpitatable valve that may be manipulated by the patient to selectively control voiding, and an inflatable balloon disposed within the patient's bladder to retain the catheter in position and minimize leakage along the exterior of the catheter. In one embodiment, the catheter body and tip are molded and a sleeve having a uniform thickness is sealed to the body to create the balloon. In another embodiment, the catheter body, tip, and balloon are molded as an integral unit using a synthetic material such as biologically compatible silicone in a manner that produces a substantially uniform balloon shape and symmetrical disposition relative to the catheter body. The balloon shape may be selectively altered by varying bonding patterns, wall thicknesses, or assembly characteristics.

The catheter body is assembled with a similarly molded discharge valve. The palpitatable valve preferably includes a multiaxial dome-type construction with a peripheral trough surrounding the dome adjacent to and displaced slightly from the wall of the valve body. The peripheral trough maximizes drainage and permits a wider valve opening. In a preferred embodiment, each valve element is separated from adjacent valve elements by an intermediate rib, and the valve elements and intermediate ribs may be readily displaced radially from the longitudinal axis of the valve by insertion of a drainage tube connector. The value elements are formed by cutting the dome while deformed to a flat configuration to create seating surfaces that are angled to increase their contact area. A retention collar is positioned on the catheter body for female patients and may be adjusted axially along helical threads to exert a desired level of tension on the catheter body to maintain the base of the balloon in contact with the interior wall of the bladder adjacent the neck and orifice. The catheter and balloon may be fabricated using a bactericidal-containing synthetic resin, coated with bactericidal or friction-reducing agents, or the balloon may be inflated with a bactericide-treated fluid that permeates the balloon. An antiseptic gel coating the threaded portion of the catheter accumulates on the proximal face of the retention collar and forms a fluid seal and barrier against migration of infectious contaminants along the exterior of the catheter, with a conical portion of the retention collar optionally being received within the distal orifice of the urethra.

BRIEF DESCRIPTION OF THE DRAWINGS

In the drawings, in which like reference numerals refer generally to corresponding elements of the various embodiments throughout the several views.

FIG. 3 is a cross-sectional view of the distal portion of the catheter body of FIG. 1 showing the intact configuration of a dome-type discharge valve;

FIG. 4 is a top cross-sectional view of a preferred embodiment of the discharge valve taken through line 4—4 in FIG. 3 showing the valve in the relaxed and closed position;

FIG. 5 is a top cross-sectional view of the discharge valve of FIG. 4 showing the valve in a deformed and open position;

FIG. 41A is a partially broken away cross-sectional view showing the components of a mold and mandril used to fabricate the catheter partially shown in FIG. 36, with the preformed tube which will define the inflation lumen already in place;

FIG. 41B is an enlarged, proximally-directed cross-sectional view of the mold, mandril and preformed tube of FIG. 41A as seen from line 41B—41B;

FIG. 42 is a partially broken away cross-sectional view of the proximal end of a urinary catheter molded within the mold of FIG. 41A showing the mandril being removed from the central lumen;

FIG. 43A is an exploded longitudinal side view of a silicone inflation balloon sleeve and the proximal portion of the catheter body of an alternate catheter of the present invention shown in partial cross-section in FIG. 44 prior to assembly thereof;

FIG. 43B is an enlarged, proximally-directed cross-sectional view of the catheter of FIG. 43A as seen from the line 43B—43B;

FIG. 44 is an enlarged, partially broken away cross-sectional view of the proximal portion of the catheter shown in FIG. 43A after it is assembled as seen from line 44—44, having a spherical balloon, partially shown in phantom when inflated;

DESCRIPTION OF THE PREFERRED EMBODIMENTS

Figure 1:
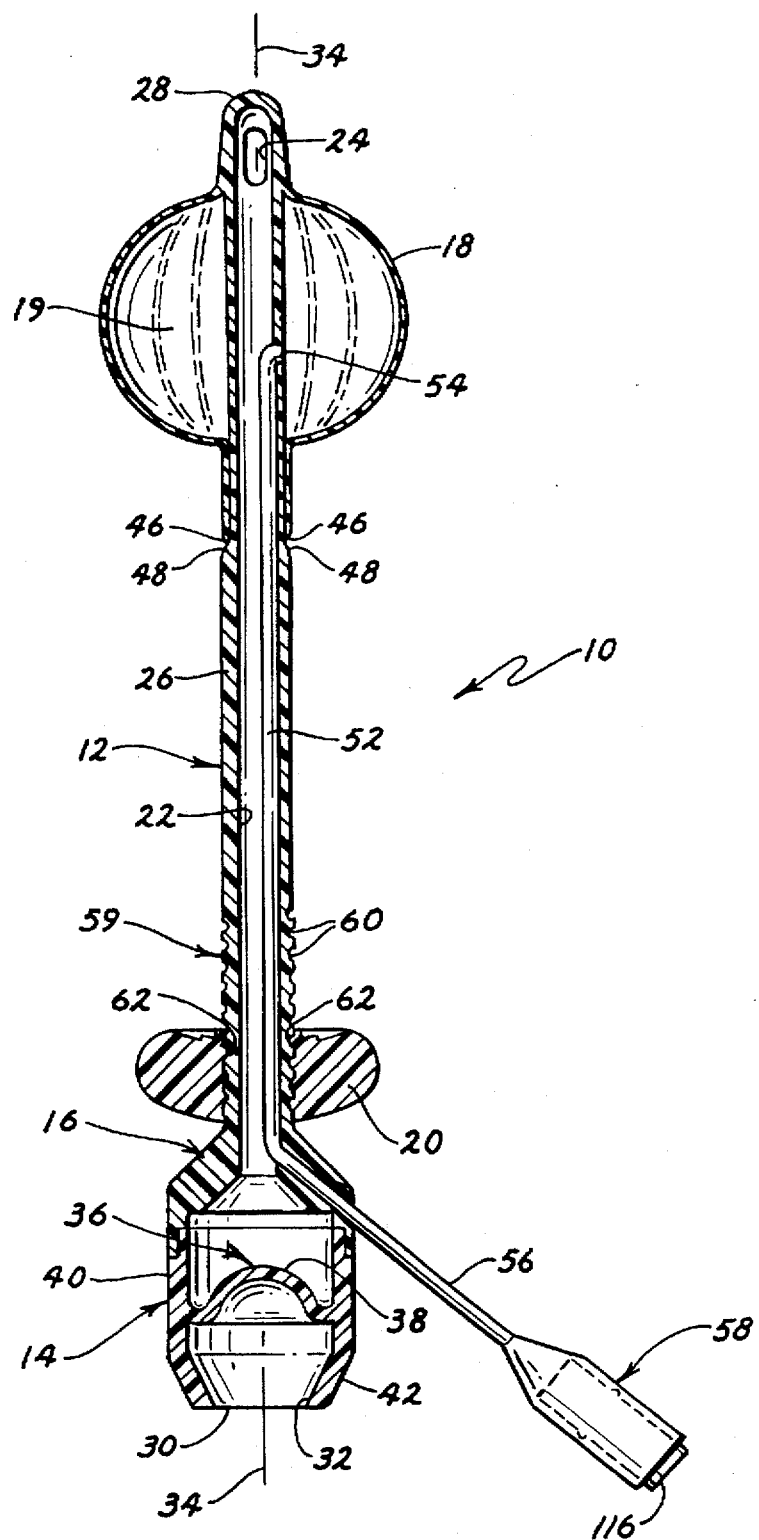
FIG. 1 is a longitudinal cross-sectional view of a urinary catheter of the present invention.

Urinary catheters of the present invention are generally shown in FIGS. 1–51 and generally referenced therein by the reference numeral 10.

Figure 2:
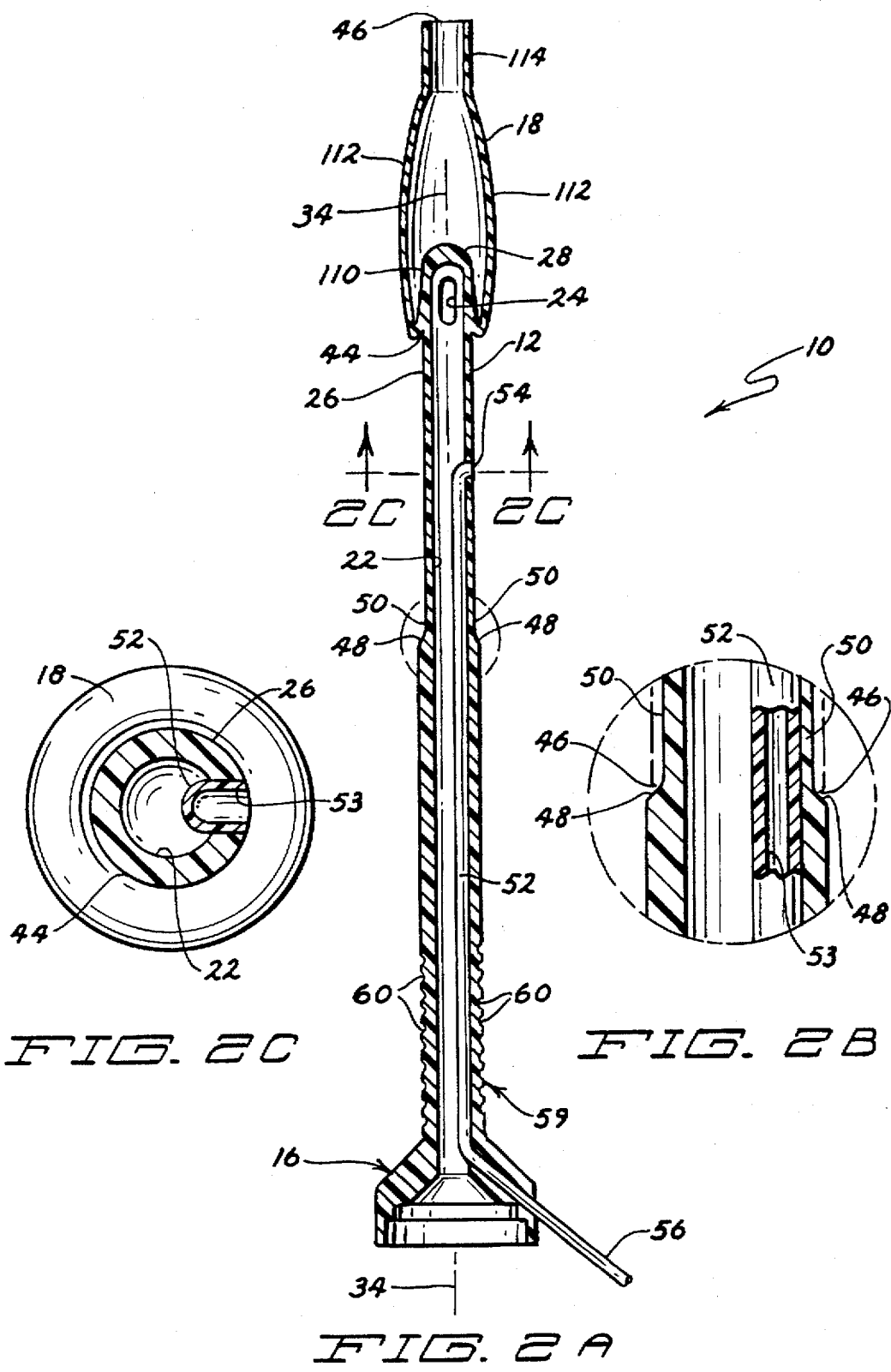
FIG. 2A is a longitudinal cross-sectional view of the proximal portion of the catheter of FIG. 1, showing the distal end of the inflatable balloon inverted relative to the catheter body.
FIG. 2B is an enlarged partially broken away detailed view of a segment of the proximal portion of the catheter body shown circled in phantom in FIG. 2A.
FIG. 2C is a proximally-directed cross-sectional view of the proximal portion of the catheter body of FIG. 1 as taken through line 2C—2C in FIG. 2A.

Referring now particularly to FIGS. 1–3, the illustrated catheter 10 includes a catheter body 12 that is composed of a distal portion 14 and a proximal portion 16 that are matingly connected as described below. An inflatable balloon 18 is connected to and extends from the catheter body 12, and a retention collar 20 is disposed around a threaded portion 59 of the catheter body 12.

The catheter body 12 defines a central lumen 22 extending from and communicating with Murphy Eye openings 24 through the side wall 26 of the catheter body 12, and a closely adjacent the proximal end 28 of the catheter body 12 to the distal end 30 of the catheter body 12 which defines a discharge opening 32. The proximal end 28 of the catheter body 12 preferably forms a partially enclosed and rounded tip of the catheter body 12, with the exception of the Murphy Eye openings 24 on the opposite sides of the catheter body 12. The catheter body 12 and central lumen 22 are further defined by a longitudinal axis consistent with broken line 34 and extending along the entire length of the catheter body 12, although the catheter body 12 may be freely flexed out of alignment with the longitudinal axis 34. Although a single opening 24 may also be utilized, including an opening 24 which intersects or overlaps the longitudinal axis 34 at the tip 28 of the catheter body 12, a plurality, preferably two openings 24, are preferred.

The distal portion 14 of the catheter body 12 defines a multiaxial palpitatable valve 36 preferably including a dome-type valve member 38 that may be moved between a normally closed position to an open position when the valve 36 is gripped and deformed. The valve 36 can be deformed by applying squeezing pressure against any two opposing sides of the valve wall 40, which also forms the side wall of the distal portion 14 of the catheter body 12.

The valve wall 40 is generally cylindrical at its proximal end, and at its distal end defines a truncated conical segment 42 having an inward radial taper terminating in the discharge opening 32. The proximal end of the distal portion 14 of the catheter body 12 defines a segment of reduced outer diameter in the valve wall 40 that permits the proximal end of the distal portion 14 to be matingly received within, and fixedly connected to, the distal end of the proximal portion 16 of the catheter body 12, with the distal end of the proximal portion 16 correspondingly defining a segment of increased inner diameter, with the distal portion 14 and proximal portion 16, preferably having the same outer diameter so as to have a flush outer surface having a generally cylindrical shape coextensive between the distal portion 14 and proximal portion 16 of the catheter body 12.

The illustrated inflatable balloon 18 is connected to, and molded unitarily at its proximal end 44 with, the proximal portion 16 of the catheter body 12 including the catheter tip 28, and is initially configured such that the distal end 46 of the inflatable balloon 18 is displaced from the catheter body 12 in an inverted configuration with the inflatable balloon 18 extending in the proximal direction away from the catheter body 12 and circumscribing the longitudinal axis 34, with a substantial portion of the balloon 18 being disposed more proximally relative to the tip 28 of the catheter body 12 as shown particularly in FIG. 2A.

The catheter body 12 defines an inwardly tapered neck 48 adjacent a seating region 50 having a diameter reduced an amount corresponding approximately to the thickness of the inflatable balloon 18, so that the inflatable balloon 18 can be inverted distally until the distal end 46 contacts the tapered neck 48 and the seating region 50 along the exterior of the catheter wall 26. The distal end 46 of the inflatable balloon 18 is bonded to the exterior surface of the catheter wall 26 along a portion of the seating region 50 using well-known bonding procedures, so as to form a flush outer surface having a generally cylindrical shape. A fluid-tight seal is therefore formed between the inflatable balloon 18 and the catheter wall 26 proximate the distal end 46 of the balloon 18 to enclosed an interior inflation region 19 within the inflatable balloon 18.

An inflation tube 52 defining an inflation lumen 53 within the catheter wall 26 extends from an opening 54 in the catheter wall 26, communicating with the interior inflation region 19 of the inflatable balloon 18, to an inflation port 58 interconnected to a proximal segment 56 of the inflation tube 52. Fluid is injected through the inflation port 58 and inflation lumen 53 to inflate the interior region 19 of the inflatable balloon 18 from a completely collapsed configuration (not shown) through two intermediate configurations shown in phantom in FIG. 1, to a completely inflated yet highly pliable or compliant configuration, which may be either a generally spherical shape as shown in FIG. 1, that is both radially and axially symmetrical, or conversely a toroidal or axially asymmetrical shape as described in further detail below.

The catheter wall 26 defines helical threads 60 along a threaded 59 thereof, with the retention collar 20 defining mating threads 62 which permit the collar 20 to be turned in increments to move axially up or down the threaded portion 59 of the catheter body 12 by rotation of the collar 20 relative to the catheter body 12.

Referring now particularly to FIGS. 1 and 3–5, a preferred embodiment of the dome-type valve 36 is shown. The valve member 38 has a generally circular ape axial cross-section as shown in FIGS. 4 and 5. The valve member 38 extends radially inward and slightly distally downward from the interior surface of the valve wall 40, and then further radially inward and generally proximally upward to an apex 66 intersecting the longitudinal axis 34, thereby forming a trough or intermediate region 68 circumscribing a generally arcuate central dome area, proximate the apex 66. The valve member having a convex surface 70 opposing the anticipated flow of fluid from the central lumen 22 and a concave surface 72 facing generally distally or downstream. The peripheral edge 74 of convex surface 70 differs from the convex surface 70 proximate the apex 66, because the convex surface 70 in the area of the peripheral edge 74 is in fact radially concave, creating a trough 75 which encircles the apex 66.

Referring now again to FIG. 2A, it may be seen that the proximal portion 16 of the illustrated catheter body 12 is molded with the inflatable balloon 18 formed integrally or as an integral part connected to and extending from the catheter body 12. The proximal tip 110 at the proximal end 28 of the catheter body 12 is also formed integrally with the proximal portion 16 of the catheter body 12 and inflatable balloon 18. The inflatable balloon 18 is initially disposed in a tubular form, with a slight bulge or curvature to the intermediate segments 112 of the side walls of the inflatable balloon 18, and a generally cylindrical seating segment 114 disposed adjacent to the distal end 46. This bulge or curvature is believed to decrease the pressure necessary to initiate inflation of the balloon 18, and lowers the eventual maximum inflation pressure needed to achieve a particular inflated shape so that the inflatable balloon 18 remains softer, more pliable, and yet stronger and more resistant to failure when fully inflated. The exterior of the catheter body 12 adjacent the proximal end 44 of the inflatable balloon 18 may be roughened or patterned to prevent the inflatable balloon 18 from adhering to any surface of the catheter body 12 it might contact prior to or during curing, when removed from the mold, or during subsequent handling.

Referring now also to FIGS. 2B and 2C, the illustrated catheter body 12 includes an inflation lumen 22 defined by a performed inflation tube 52. In preferred embodiments to preformed inflation tube 52 and the catheter body are made of silicone rubber. A preferred inflation tube 52 is 80 durometer silicone rubber and the molded catheter body 12 is 50 durometer silicone rubber.

Following the molding process, the inflatable balloon 18, of the illustrated catheter body 12 shown in FIG. 2A, is folded distally until the distal end 46 is adjacent to and contacting and engaging the inwardly tapered neck 48 of the catheter body 12. The distal end 46 of the inflatable balloon 18 is fixedly and sealingly attached to the catheter body 12 using an adhesive bond between a predetermined portion of the seating segment 114 and the exterior surface of the catheter body 12 within the seating region 50. In preferred embodiments made of silicone rubber, the adhesive is a Q74840 two-part medical grade silicone adhesive from Dow Chemical Co. in Midland, Mich. The length of the bond within the seating segment 114 measured between its proximal and distal ends, and the distance between the distal end 48 or tapered neck 48 and the most proximal end of the inflatable balloon 18 when it is partially and fully inflated. For example, extending the bond proximally can produce an axially asymmetrical balloon shape. the ultimate shape and axial symmetry of the inflatable balloon 18 when inflated will depend upon the length of the inflatable balloon 18 between its proximal 44 and distal 46 ends, the thickness and uniformity of the intermediate segments 112 of the side walls of the inflatable balloon 18, and the length, position, displacement, and uniformity of the bond within the seating segment 114.

Referring now to FIGS. 14, 15, 18, and 19, it will be appreciated that the axial (and radial) symmetry or asymmetry of the inflatable balloon 18 may be affected in a controlled manner by altering the thickness of the proximal end 44, distal end 46, or intermediate segments 112 of the side walls of the inflatable balloon 18 and the inflation pressure to form a virtually limitless variety of shapes and configurations. Some more conventional shapes may include ovoidal (axial length greater than radial diameter), spheroidal (axial equalling radial diameter), toroidal (radial diameter greater than axial length), pear (proximal end radially larger than distal end), and tear (distal end radially larger than proximal end.)

Figure 14:
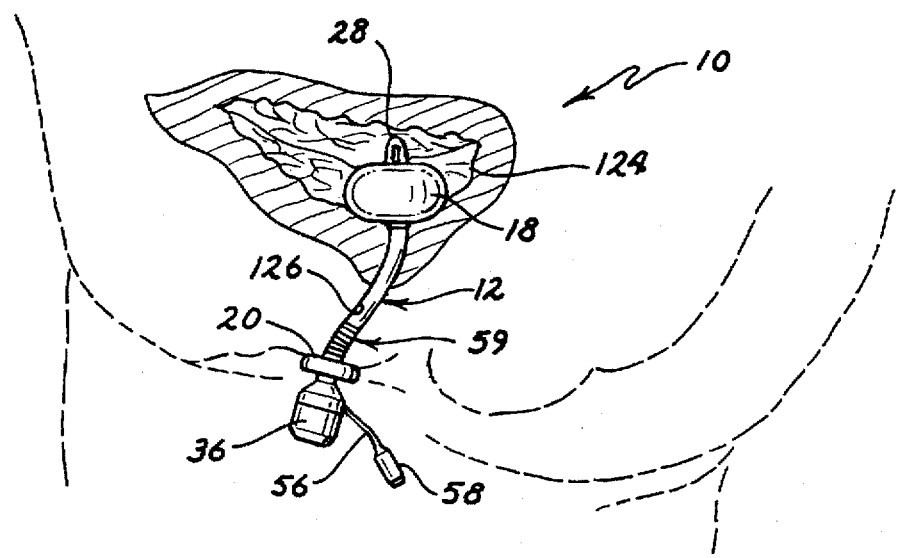
FIG. 14 is a partial anatomical side-sectional view of the urinary tract of a female patient showing an alternate catheter of the present invention implanted therein, the catheter having a toroidal balloon and a retaining collar.
Figure 15:
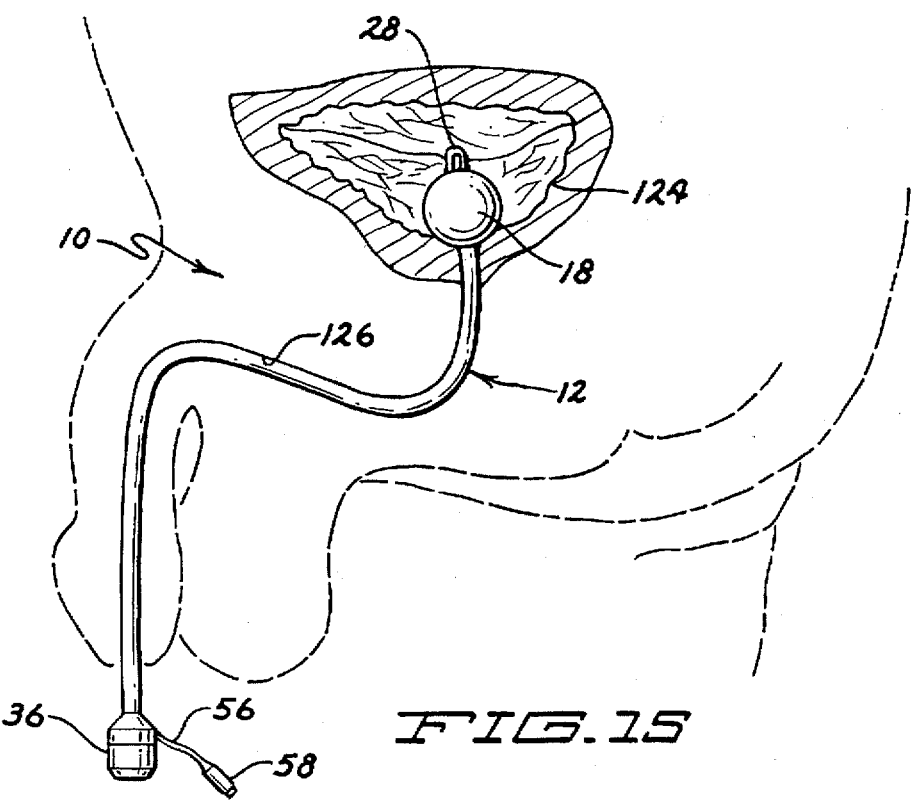
FIG. 15 is a partial anatomical side-sectional view of the urinary tract of a male patient generally showing an alternate catheter of the present invention implanted therein, the catheter having a generally spherical balloon.
Figure 18:
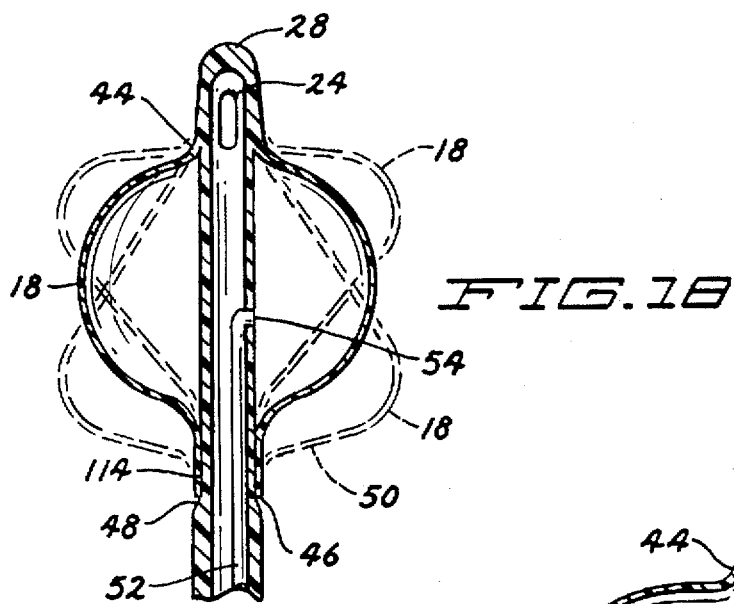
FIG. 18 is a side cross-sectional view of the upper portion of the catheter body and generally spherical balloon of FIG. 1, with two alternate embodiments of the balloon shape shown in phantom.
Figure 19:
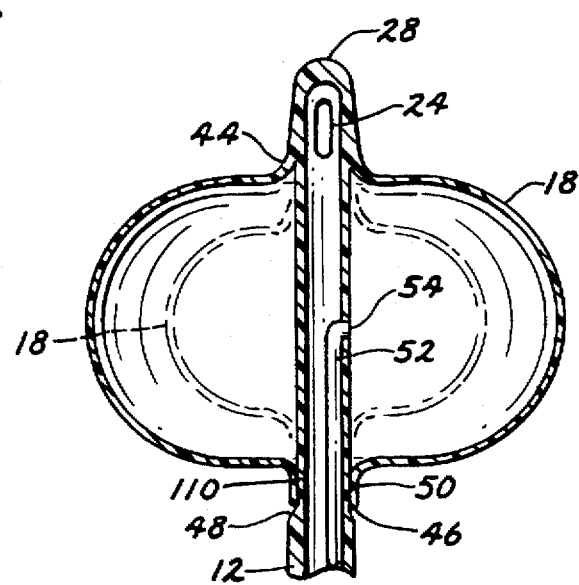
FIG. 19 is a side cross-sectional view of the upper portion of the catheter body and generally toroidal balloon of FIG. 14, with one alternate embodiment of the toroidal balloon shape shown in phantom.

A generally spherical configuration for the inflatable balloon 18 is believe preferable for male patients as shown in FIGS. 15 and 18. Conversely, a toroidal shape is believed preferable for female patients as shown in FIGS. 14 and 19. The toroidal shape may be obtained by inflation of the inflatable balloon 18 to a generally toroidal shape, or as shown in phantom by increasing the wall thicknesses of the inflatable balloon adjacent the proximal end 44 and the distal end 46 (as well as increasing the length of the bond between the seating segment 114 and seating region 50) to produce a toroidal effect.

Referring now particularly to FIG. 18, a combination of increasing wall thickness of the inflatable balloon 18 in selected regions and adjusting the length and placement of the bond between the seating segment 114 and seating region 50 can be utilized to produce axially asymmetrical configurations for the inflatable balloon 18, such as are shown in phantom in FIG. 18.

Figure 20:
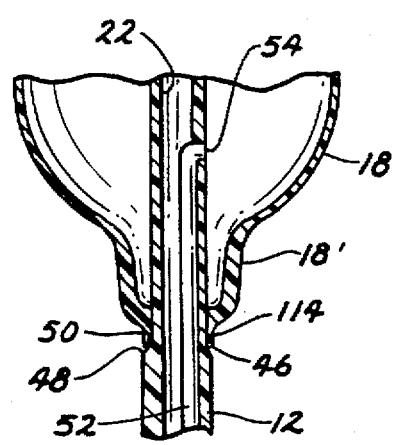
FIG. 20 is a side cross-sectional view of the upper portion of an alternate catheter body and balloon, wherein the base of the balloon forms a generally cylindrical stepped segment having a diameter greater than that of the catheter body and less than the maximum diameter of the balloon.

Referring now particularly to FIG. 20, more complex shapes such as a stepped configuration for the inflatable balloon 18 may be achieved by varying the wall thickness of the inflatable balloon 18 and the length and placement of the bond between the seating segment 114 and seating region 50. In the stepped configuration of FIG. 20, a first region of the inflatable balloon 18' has a slightly thicker wall than the remainder of the inflatable balloon 18, resulting in a generally cylindrical region of decreased diameter compared with the uniform curvature of a spherical balloon 18 when inflated. The potential shapes and configurations for the inflatable balloon 18 which may be achieved are virtually limitless given different thicknesses of the wall of the inflatable balloon 18, patterns of varying thickness that can be molded into the interior or exterior surfaces of the inflatable balloon, the bonding pattern, and the inflation pressure. It will be appreciated that the molding and bonding processes described will permit configurations, orientations, and varying wall thicknesses for an inflatable balloon 18 that cannot be achieved using conventional dipping, masking, and stripping process known to the art.

It should be noted that the inflatable balloon 18 is initially formed with the intermediate segments 112 of the side walls slightly curved or bowed to minimize the inflation pressure initially required to induce inflation. Some physicians may prefer this configuration for insertion of the catheter body 12, whereas others may prefer to draw a vacuum and retract the inflatable balloon 18 to a completed deflated and collapsed configuration (not shown).

In preferred embodiments of the present catheter 10, the inflatable balloon 18 has either a generally spheroidal or generally toroidal shape in which the thickness of the side walls of the inflatable balloon 18 is substantially uniform along each path circumscribing the inflatable balloon 18 formed at each axial segment along the longitudinal length of the inflatable balloon 18, and over the entire surface area of the inflatable balloon 18, such that the inflatable balloon 18 is uniformly and symmetrically shaped and disposed in radial symmetry relative to the longitudinal axis 34 of the catheter body 12.

Figure 36:
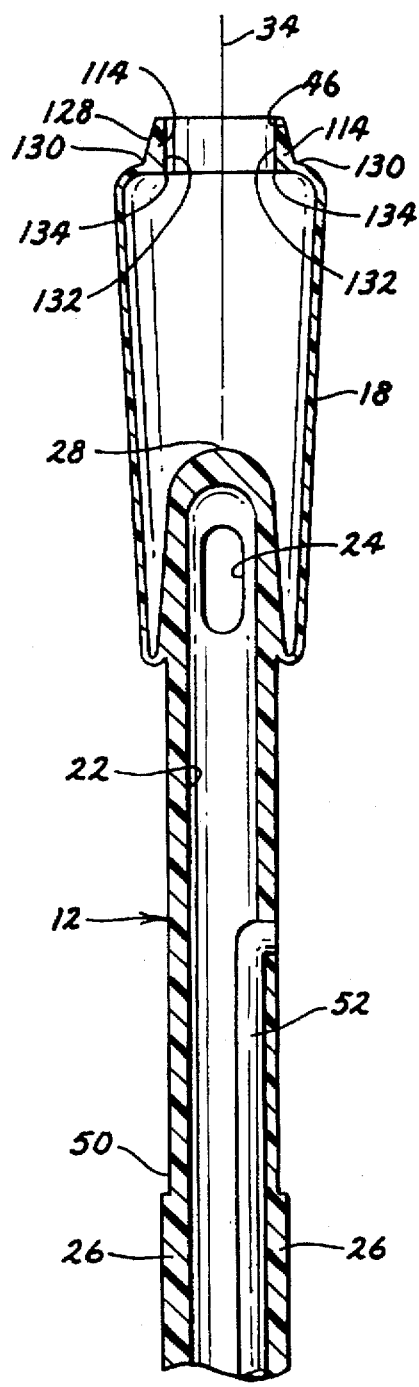
FIG. 36 is a partially broken away side cross-sectional view of an alternate embodiment of the inflatable balloon and catheter body of the catheter shown in FIG. 1 with the balloon in an inverted configuration.
Figure 37:
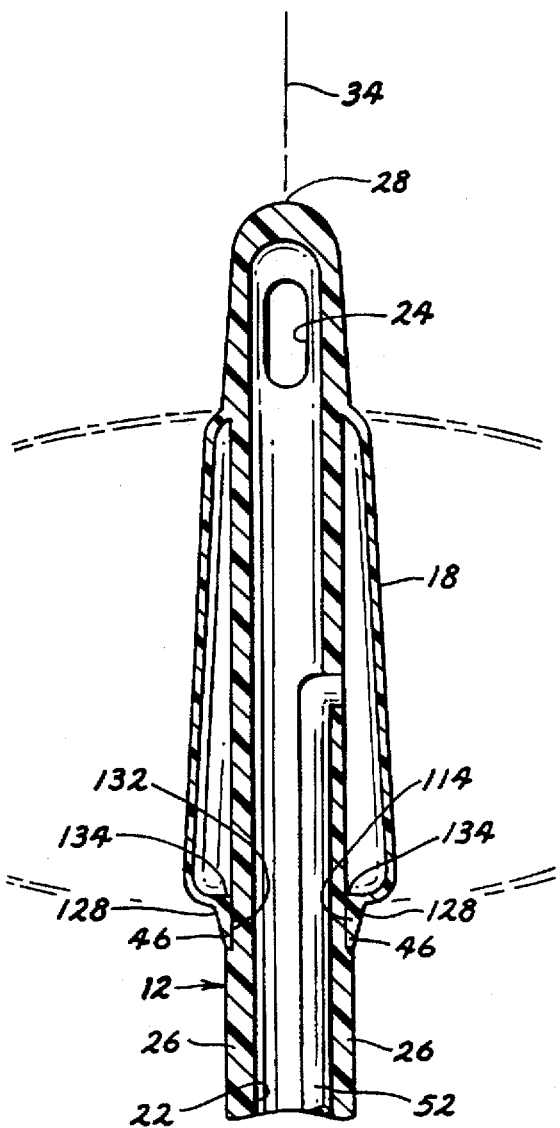
FIG. 37 is a partially broken away side cross-sectional view of the alternate embodiment of the inflatable balloon and catheter body of FIG. 36 with the projecting segment forming a truncated conical surface extending radially from the catheter body adjacent the distal end of the balloon.

Referring now to FIGS. 36 and 37, an alternate embodiment of the present catheter body 12 as illustrated. A toroidal shaped inflatable balloon 18 is molded such that the distal end 46 of the inflatable balloon 18 defines a tapered segment 128 throughout the length of the cylindrical seating segment 114, such that the outer surface forms an angular junction 130 with the bottom of the inflatable balloon 18 along the exterior, and the inner surface 132 remains generally parallel with the surface of the side wall 26 to provide a bonding surface. The inner surface 132 similarly forms and angular junction 130 with the inflatable balloon 18, such that the inflatable balloon 18 extends from the tapered segment 128 at an angle generally perpendicular to the longitudinal axis 34 of the catheter body 12. The tapered segment 128 thereby forms a non-inflatable truncated conical sealing member that may be received within the neck or orifice of the bladder 124 to further minimize leakage, but which does not change its shape or diameter when the inflatable balloon 18 is inflated and also does not affect the otherwise toroidal or spherical shape of the inflatable balloon 18 when in a fully inflated configuration. Because the tapered segment 128 and angular junction s 130, 134 orient the wall of the inflatable balloon 18 towards perpendicular to the longitudinal axis 34 of the catheter body 12 at the bottom of the balloon 18, the tapered segment 128 and angular junctions 130, 134 ensure that the bottom annular surface of the inflatable balloon 18 contacting the bottom wall of the bladder 124 will be general coplanar and parallel with the inner horizontal surface of the bladder 124 surrounding the neck and orifice of the bladder 124. However, it should be noted that this embodiment increases the effective diameter of the catheter body 12 when the inflatable balloon 18 is initially deflated for insertion through the urethra 126.

Other complex shapes for the inflatable balloon 18 may also be produced using the molding process involving varying wall thicknesses and initial configurations. For example, it is anticipated that one useful configuration would be a balloon having a "mushroom" or "umbrella" shape, oriented in either an upright or inverted configuration with the catheter body 12 as the stem or handle, that is radially symmetric but has axially overlapping portions. Another useful configuration would include "projections" or "fingers" that extend radially outward and axially at a distal or proximal angle relative to the catheter body 12, providing an inflatable anchoring configuration similar to that produced by mechanical or articulated anchors described in the prior art. The advantages of such configurations include decreased inflation volumes, lower inflation pressures, small seating areas adjacent the neck and orifice of the bladder 124 (to reduce instances where drainage or normal movement of the bladder 124 causes contact between the inflatable balloon 18 and wall of the bladder 124 that would otherwise dislodge the inflatable balloon 18), more pliable side walls of the inflatable balloon 18 that would prevent contact with the wall of the bladder 124 from a transverse radial direction from placing undue axial tension on the catheter body 12 due to pivoting the inflatable balloon (causing both leakage and pain to the patient), and to promote increased drainage and retraction of the bladder 124.

Figure 17:
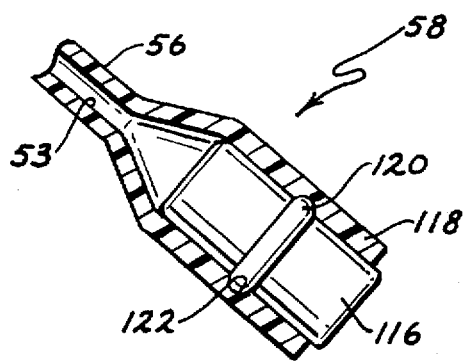
FIG. 17 is an enlarged partially broken away cross-sectional view of one embodiment of the inflation port of FIG. 1.

Referring now specifically to FIGS. 1 and 17, it will be appreciated that the injection port 58 is preferably fabricated by inserting or receiving a conventional Halkey-Roberts type valve 116 into a molded retainer 118 attached in fluid communication with the intermediate tube 56 and inflation lumen 52. The Halkey-Roberts type valve 116 may have the retainer 118 molded around the exterior thereof, or the Halkey-Roberts type valve 116 may be pressure fit within the retainer 118 and secured in place by an annular projection 120 that engages within a corresponding groove 122 defined by the interior of the retainer 118. A self-sealing silicone valve may also be utilized in place of the Halkey-Roberts type valve 116 to enhance the aesthetic appearance and reduce the size of the exposed portions of the particular catheter 10. However, care must be taken not to puncture or damage the self-sealing valve or the entire catheter 10 is rendered useless.

The inflation lumen 52 can be molded as an integral part of the catheter wall 26 in the proximal portion 16 of the catheter body 12 by inserting a removable wire within the mold along the predetermined path of the inflation lumen, or can be fabricated by placing a corresponding diameter tube within the mold extending between the position of the opening 54 and the injection port 58. The intermediate tube 56 preferably exits the proximal portion 16 of the catheter body 12 at an angle relative to the longitudinal axis 34 and proximal to the seam between the distal portion 14 and proximal portion 16 of the catheter body 12, as to permit fabrication and cutting of the valve 36 as a separate component, and to prevent the intermediate tube 56 or injection port 58 from interfering with the palpitation of the valve 36 or the discharge of urine from the discharge opening 32. It will further be appreciated that the valve openings 76 are preferably cut through the valve member 38 prior to the distal portion 14 of the catheter body being engagingly mounted and bonded (or otherwise fixedly attached) to the proximal portion 16 of the catheter body 12 to form a complete unitary catheter 10.

Referring now particularly to FIGS. 1 and 38-40, it will be appreciated that the retention collar 20 is molded as a separate unit and mounted on the catheter body 12 prior to insertion of the catheter body 12 within the patient. The collar 20 may be mounted either before or after the distal end 46 of the inflatable balloon 18 has been secured to the catheter body 12, but prior to its inflation. The relative position of the collar 20 along the length of the catheter body 12 is adjusted by rotating the collar 20 relative to the catheter body 12. With helical threads 60 having a constant and uniform pitch, the axial movement of the collar 20 relative to the catheter body 12 will be generally proportional to the relative number of revolutions or the degree of angular rotation between the collar 20 and catheter body 12. Rotation in one direction will move the collar 20 proximally along the catheter body 12, and rotation in the opposite direction will move the collar distally.

Figure 38:
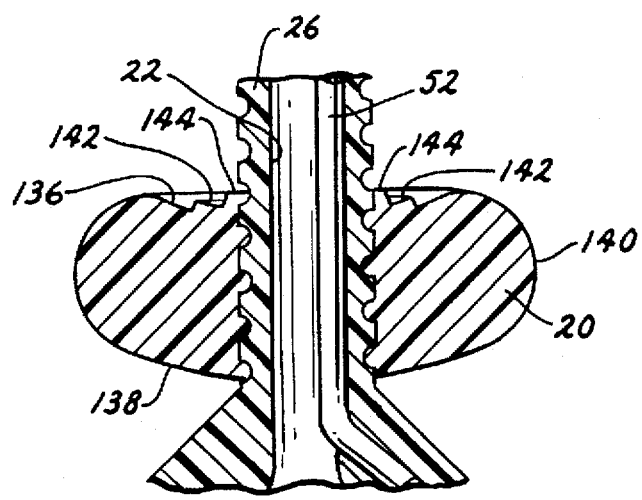
FIG. 38 is a partially broken away side cross-sectional view of an embodiment of the catheter body and collar of the present invention showing first and second tiers on the concave top surface of the collar.

FIGS. 1 and 38 show a collar having a generally curved shape with a concave top surface 136, convex bottom surface 138, and a uniformly radiused peripheral surface 140. The peripheral surface 140 may be knurled, patterned, or roughened to provide extra purchase when gripped for adjustment. The concave top surface 136 defines a two-tiered configuration, including a first annular tier 142 sized and designed to exert radial pressure against the labia minora of a female patient, and a second annular tier 144 sized and designed to exert axial pressure surrounding the external orifice of the urethra 126 (or conversely inserted within the orifice of the urethra 126 if desired.)

Figure 39:
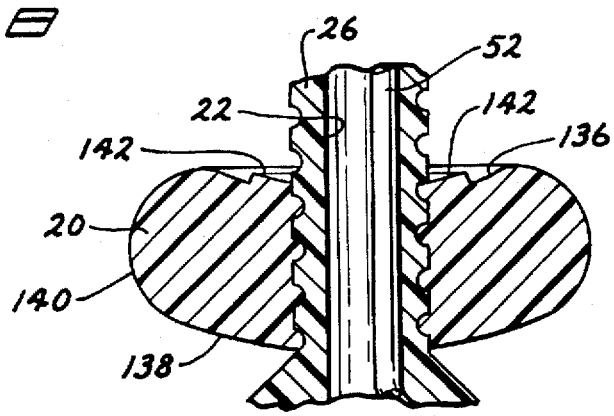
FIG. 39 is a partial side cross-sectional view of a further embodiment of the catheter body and collar of the present invention showing a single tier on the concave top surface of the collar.
Figure 40:
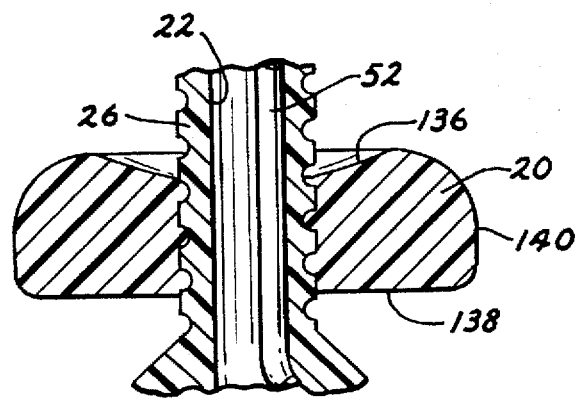
FIG. 40 is a partial side cross-sectional view of yet another embodiment of the catheter body and collar of the present invention showing a concave top surface and a generally planar bottom surface on the collar.

FIG. 39 shows an alternate embodiment of the retention collar 20 shown in FIG. 38, wherein only the first annular tier 142 is present. It will be appreciated that a similar embodiment having only the second tier 144 could be fabricated. FIG. 40 shows a third embodiment in which the top surface 136 is concave as with the embodiments shown in FIGS. 1, 38, and 39, but wherein the bottom surface 138 is generally planar and oriented in a plane which is generally perpendicular to the longitudinal axis 34 of the catheter body 26 with the concave top surface 136 facing proximally toward the patient, or may invert the collar 20 such that the planar bottom surface 138 faces proximally toward the patient.

Figure 45:
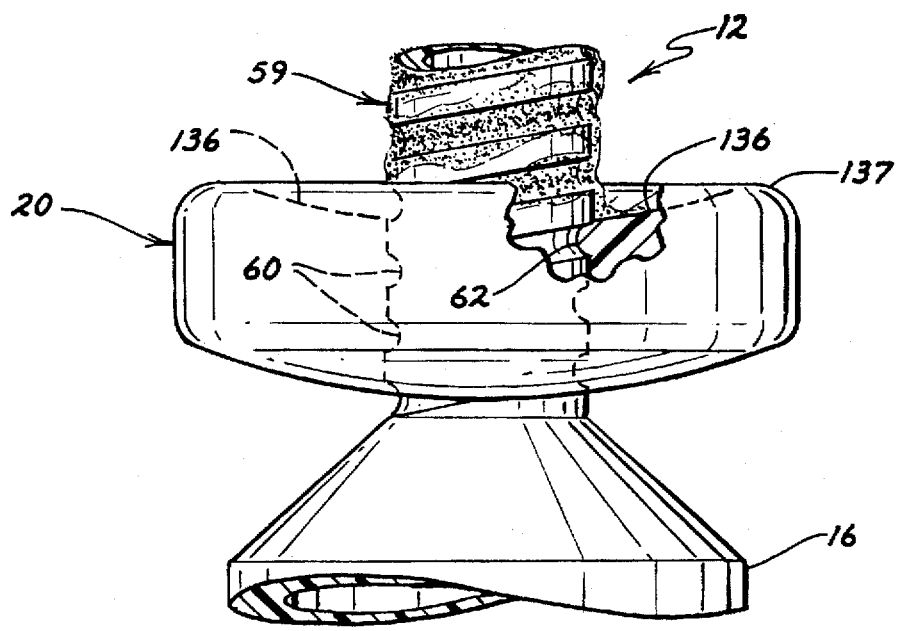
FIG. 45 is a partially broken away side view of a preferred retention collar of the present invention having a concave top surface.
Figure 46:
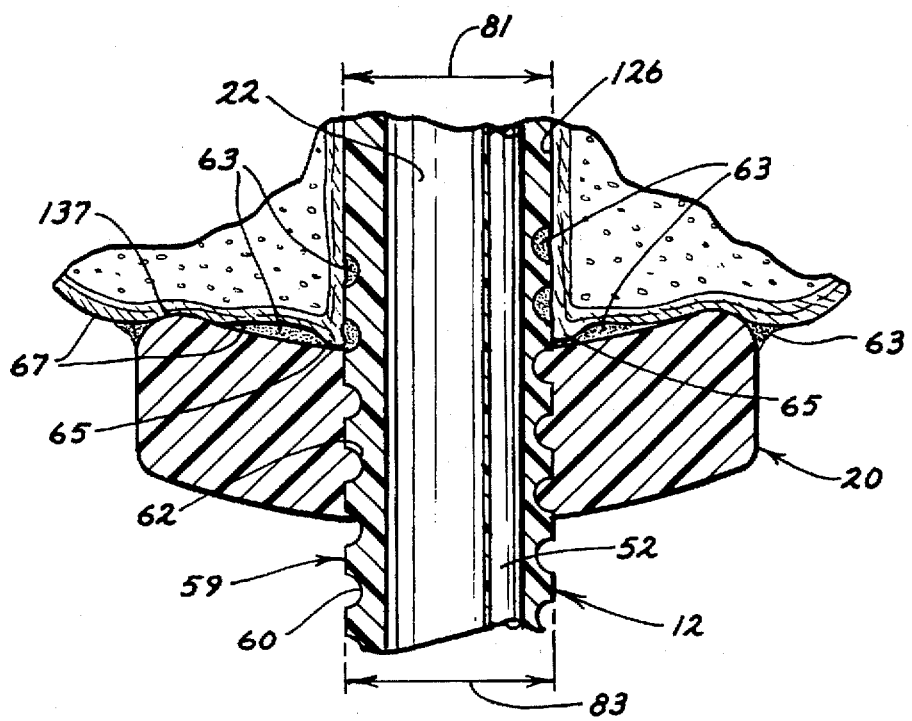
FIG. 46 is a partial anatomical cross-sectional view of the threaded portion of a catheter body of the present invention with the preferred retention collar of FIG. 45 in a proximal position adjacent an area of tissue surrounding the distal orifice of the urethra, with the antiseptic gel forming a fluid seal and a barrier to the migration of infectious agents along the exterior of the catheter body through the distal orifice of the urethra.

Referring now also to FIGS. 45 and 46, a preferred retention collar 20 is shown. This collar 20 has a top surface 136 which is concave such that when the peripheral edge 137 of the illustrated collar 20 is drawn up against the surface area 67 surrounding the urethral orifice 65 the peripheral edge 137 presses against the surface area 67 to create a tension up on the catheter body 12 which, in turn, draws the balloon 18 against the neck and orifice of the interior of the bladder 124 when the catheter 10 is inserted in a female patient as shown in FIG. 14. The illustrated concave surface 136 allows the pressure or force exerted against the surface area 67 to be concentrated proximate the peripheral edge 137 and away from the urethral orifice 65, which is very sensitive to such force.

While the direction of relative rotation of the retention collar 20 may be selected as desired, it is deemed advantageous to have a collar 20 move proximally when the catheter body 12 is gripped by the left hand adjacent the valve 36 and the collar 20 is rotated clockwise by the right hand. It will be appreciated that a collar 20 will not be used in all applications, and will preferably be utilized with female patients, because female patients generally have shorter urethral lengths and greater need for supplemental anchoring or protection against jarring or displacement of the inflatable balloon 18 when drawn against the neck and orifice of the bladder to prevent urine leakage around the catheter.

The combination of helical threading 60 and mating threading 62 may include helical threading 60 disposed on the catheter body 12 and a non-helical mating thread 62 such as an annular projection or ring extending radially inward from the bore of the collar 20, or mating helical threading 60 on both the catheter body 12 and within the bore of the retention collar 20.

Referring now particularly to FIGS. 14 and 15, the catheter 10 of this invention is shown implanted in a conventional manner within the bladder 124 and urethra 126 of a male and female patient, respectively. It will be appreciated that in a male patient, the use of a collar 20 is not as likely to provide a suitable option for tensioning the catheter body 12 and inflatable balloon 18. One alternative to the use of a collar 20 is an inflatable member (not shown) disposed adjacent to the exterior of the bladder 124, and another option is to increase the length of the catheter 10 to provide sufficient excess catheter body 26 external to the patient to minimize dislodgement.

Due to the natural permeability of the silicone material from which the preferred inflatable balloon 18 is formed, the fluid (usually physiological saline) used to inflate the inflatable balloon 18 may be treated with an aliquot of a therapeutic agent bactericidal or microbicidal agent that will diffuse through the inflatable balloon 18 into contact with urine within the bladder 124, or alternately will contact urine which diffuses through and into the interior of the inflatable balloon 18. Instead of a bactericidal agent, other therapeutic compounds could be utilized, such as steroids, anti-inflammatory agents, or other medications designed to treat specific conditions.

In addition, because infections tend to migrate or gravitate up the catheter body 12 and urethra 126 toward the bladder 124, the bore and proximal face of the collar 20 and surrounding portion of the catheter body 12 may be coated with an anti-bactericidal or anti-microbicidal agent 63 in a gel or liquid form. Alternately, the material from which the catheter body 12 is fabricated may be impregnated with a predetermined concentration of a bactericidal agent such as silver. The catheter body 12 may also be coated with friction-reducing agent such as Teflon®, a silicone having a different durometer hardness than the catheter body 12, or various other biocompatible materials selected for their known and intended physiological properties.

In a representative embodiment for female patients as shown in FIGS. 1, 2, and 14, the catheter 10 has an overall length of between about 4" and 5" measured between the proximal end 28 and distal end 30, and the inflatable balloon 18 has a relaxed wall thickness of 0.010" compared to a wall thickness for the catheter body of 0.035". The helical threading 60 has alternating lands 134 and grooves 136, with lands 134 of 0.040" width separating ovoid section grooves 136 having a width of 0.040" and a depth of 0.020" or slightly greater. The distal one third of the seating segment 114 is bonded to the catheter body 12, and the entire exposed mating surfaces of the reduced diameter segment 130 and recessed portion 132 are bonded together. It may be readily appreciated that the dimensions of the various components of the catheter 10 will be determined based upon conventional anatomical measurements, and various sizes and shapes for these components will be required to accommodate patients with different anatomical characteristics.

Referring now again to FIGS. 45 and 46, an embodiment of the threaded region 59 of the illustrated catheter body 12 and a retention collar 20 are shown in which an antibacterial or other antiseptic substance 163 such as abetadine-containing gel is initially disposed within the helical threading 60 of the catheter body 12. The mating threading 62 of the retention collar 20 received within the recess formed by the helical threading 60 displaces the antiseptic substance 63 as the retention collar is moved proximally upwardly along the illustrated catheter body 12, such that the antiseptic substance 63 moves to and accumulates on the concave top surface 136 of the retention collar 20. As the top surface 136 of the retention collar 20 is moved into close confronting proximity to, or contact with, the area of tissue 67 surrounding the distal orifice 65 of the urethra of the patient, the accumulation of antiseptic substance 67 on the concave surface 136 of the retention collar 20 contacts and is compressed against the area of tissue 67. The antiseptic substance 63 thereby fills voids formed between the concave surface 136 of the retention collar 20 and the area of tissue 67 surrounding the distal orifice 65 of the urethra, thereby forming a barrier preventing or minimizing the migration of infectious agents such as bacteria through the orifice of the urethra 65 and proximally along the exterior of the catheter body 12 within the urethra 65, and further forms a liquid seal preventing the egress or leakage of urine from within the urethra 126 through the orifice of the urethra 65 along the exterior of the catheter body 12. Additional quantities of the antiseptic substance 63 may subsequently be added.

Referring again to FIGS. 38 and 46, the concave surface 136 of the illustrated retention collar 20 may optionally define a generally conical projection 144 extending axially from the conical surface 136 proximally toward the urethra 126 and the area of tissue 67 surrounding the orifice of the urethra 65 of the patient. This projection 144 is received within the orifice of the urethra 65 a distance on the order of no more than 5 mm, and preferably on the order of 1–3 mm, when the retention collar 20 is in close confronting contact with the area of tissue 67 surrounding the orifice of the urethra 65, the projection 144 having a diameter such that the outer surface of the projection 144 contacts the interior of the urethra 126 generally proximate to the distal orifice thereof to provide an additional sealing contact against leakage or the migration of infectious agents along the exterior of the catheter body 12 within the urethra 126, but preferably does not exert undue pressure radially outward against the urethra 126 so as to create discomfort for the patient or injure the tissue forming the urethra 126.

Also shown in FIG. 46 is a comparison of the preferred relative dimensions of the shaft of the catheter body 12 located proximate the threaded region 59 and of the threaded region 59. In preferred embodiments, the shaft of the catheter body 12 has a shaft diameter 81 which is equal to or greater than the threaded region diameter 83. In this way, the insertion of the thread region 59 of the catheter 10 in the urethra will not require any further enlargement of the urethral passage wall than is already required upon the prior insertion of the shaft of the catheter body 12 proximal to the threaded region 59.

Each element or component of the catheter 10 is preferably fabricated from a synthetic material such as biologically compatible such as silicone, Kraton®, and the like, and assembled using an appropriate biologically compatible adhesive that withstands the temperature and exposure to bodily fluids associated with an indwelling catheter 12 that is used for extended periods of time. Suitable adhesives are known to the art and their selection is a matter of simple design choice. When silicone is selected as the material for molding the catheter body 12 and inflatable balloon 18, a durometer hardness of about 50 for the balloon inflatable 18, about 70 for the catheter body 12, and about 45–70 for the valve 36 have proven suitable.

Due to the pliability of the materials used to fabricate the catheter 10, a removable reinforcing member (not shown) in the form of a generally straight rod or tube having a radiused tip that is received within the central lumen 22 may be require to provide sufficient stiffness or rigidity to permit insertion of the catheter 10.

A wide variety in the selection of valves 36 and valve member 38 configurations, tolerances, dimensions, hardnesses, materials, and adhesives compared to the representative examples shown and discussed above can be made by those of ordinary skill in the art when fabricating and assembling a urinary catheter 10 according to the teachings set forth herein.

Referring now particularly to FIGS. 41A, 41B and 42, one embodiment of a mold 146 is shown for fabricating the urinary catheter 10 illustrated in FIGS. 36 and 37. The urinary catheter 10 is molded such that it is initially configured with the distal end 46 of the inflatable balloon 18 displaced from the catheter body 12 in an inverted configuration with the inflatable balloon 18 extending in the proximal direction away from the catheter body 12 as previously shown in FIG. 36. A substantial portion of the balloon 18 is disposed more proximally relative to the tip 28 of the catheter body 12 similar to that shown particularly in FIG. 2. The mold 146 includes a first half 148 and second half 150 which mate to form a hollow interior cavity 152 corresponding to the external shape and configuration of the illustrated urinary catheter 10 when molded. A first inner segment 154 and a second inner segment 156 are received within the interior cavity 152 and spaced apart therefrom in a uniform manner to define the wall thickness of the inflatable balloon 18 and the proximal tip 28 of the catheter body 12, with a portion of the interior cavity 152 communicating with the exterior of the mold 146 such that the liquid resin used to form the urinary catheter 10 may be injected within the interior cavity 152. A mandril 158 is similarly inserted within the interior cavity 152 and spaced apart therefrom in a uniform manner to define the wall thickness of the catheter body 12 and the diameter of the central lumen 22. The mandril 158 includes a number of projections 160 equal to the number of Murphy Eye openings 24 anticipated through the distal tip 28 of the catheter body 12, each projection 160 having an angled or bevelled face 162 mating with a corresponding surface or face of the first inner segment 154 or a second inner segment 156, respectively.

Figure 32:
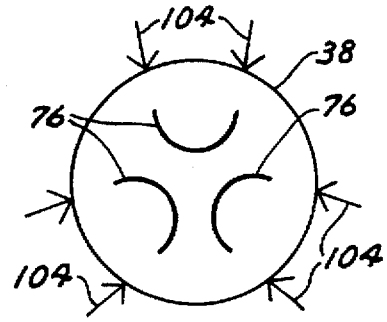
FIG. 32 is a diagrammatic view of a dome-type valve having three curved slits of generally equal radii that convexly confront and are equidistantly spaced apart from one another.

In the embodiments shown in FIGS. 41A, 41B and 32, the mandril 158 includes a longitudinal groove 159 extending longitudinally along a portion of the length of the mandril 158 to accommodate a preformed tube 52 which is incorporated into the mold 146 to provide an inflation lumen 53 in the molded catheter 10. The tube 52 extends out of the mold 146 near the base and in a more proximal position toward the inner segments 154 and 156. Once the mandril 158 and the tube 52 are in place within the mold 146, the mold 146 is sealed and polymeric material, preferably silicone rubber, is injected into the mold under pressure, preferably about 2000 psi. In preferred embodiments, the tube 52 is made of silicone rubber and has a durometer of about 80, and silicone rubber is used to make the molded portions of the catheter 10. The molded portions preferably have a durometer of about 50 and a 40 durometer silicone rubber adhesive is used to seal the balloon 18 to the seat area 50 of the catheter body 12, and the value 36 to the catheter body 12. Prior to sealing the balloon 18 to the seat area 50, a cutting tool (not shown) is used to remove the portion of the tube 52 which extends beyond the side wall 26 of the catheter body 12 when the catheter body 12 is removed from the mold 146. The edge of the tube 52 at the opening 54 of the inflation lumen 53 into what will become the interior inflation region 19 of the finished catheter 10 shown in FIG. 37, will preferably be flush with the side wall 26 of the catheter body 12 once the portion of the tube 52 extending beyond the side wall 26 is removed.

Once the urinary catheter 10 has been molded and cured appropriately within the mold 146, the first half 148 and second half 150 of the mold 146 are separated. The first inner segment 154 and a second inner segment 156 may be separated or pivoted apart from one another and withdrawn from the interior of the inverted inflatable balloon 18 with the distal ends riding over the projection 160. The mandril 158 is then withdrawn through the central lumen 22 as shown in FIG. 42, with the projections 160 stretching or deforming the material forming the catheter body 12 as the mandril 158 is withdrawn. Once the mandril 158 is withdrawn, and the projections 160 pass, the central lumen 22 returns to the unstretched or relaxed configuration of the urinary catheter 10 illustrated in FIGS. 36 and 37. Conversely, the mandril 158 could in some instances be withdrawn prior to the first inner segment 154 and a second inner segment 156 being removed from the interior of the inverted inflatable balloon 18, with the first inner segment 154 and a second inner segment 156 of the mold 146 riding over the projections 160 on the mandril 158. It will be appreciated that the placement and configuration of the projections 160 forming the openings 24 in the proximal tip 28 of the urinary catheter 10 may be adapted or constructed in a variety of ways other than the representative example shown herein.

Figure 47:
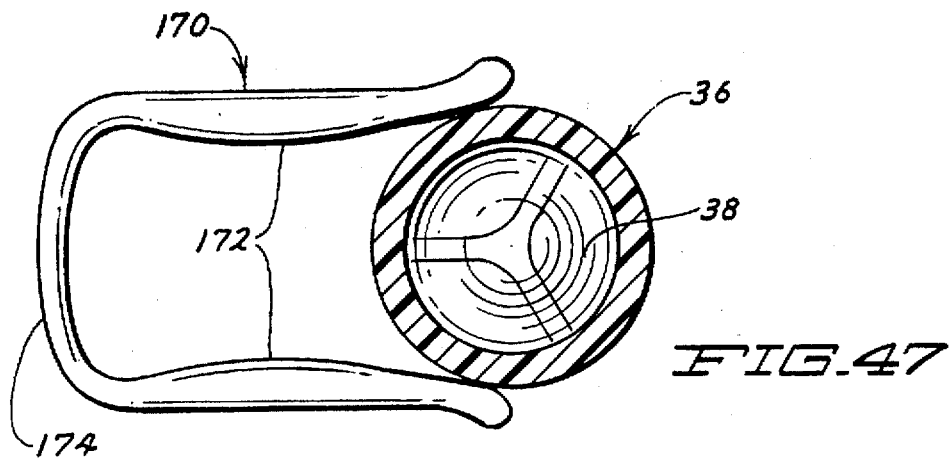
FIG. 47 is a partial cross-sectional view of the valve body of FIG. 4 directed distally showing a clip member in close proximity thereto prior to engagement with the valve body.
Figure 48:
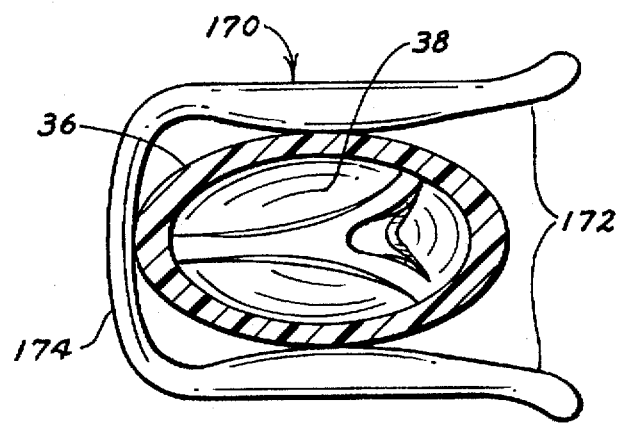
FIG. 48 is a partial cross-sectional view of the valve body of FIG. 3 directed distally showing a clip member engaged with the valve body and deforming the valve member to an open configuration similar to that shown in FIG. 5.
Figure 49:
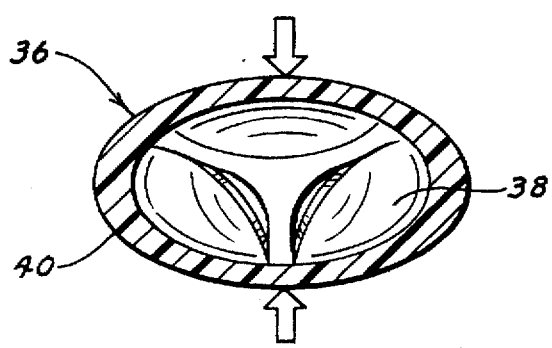
FIG. 49 is a cross-sectional view of the valve body of FIG. 4 deformed in another open configuration.
Figure 51:
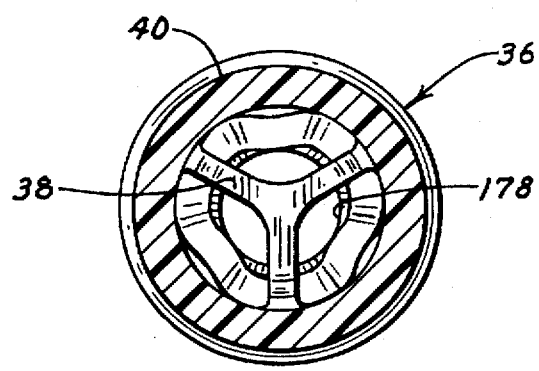
FIG. 51 is a distally-directed cross-sectional view of the valve body of FIG. 50 as seen from line 51—51 showing the tip of the connector engaged within the valve body to hold the valve member in yet another open configuration.

Referring to FIGS. 47 and 51, it will be appreciated that in some instances it will be desirable for a patient to hold the palpitatable valve 36 in the open position with the valve member 38 deformed for extended periods of time to permit drainage, in which case the provision of a releasable clip member 170 to maintain the valve 36 in the open position will be suitable. One embodiment of such a clip member 170 is shown in which a generally U-shaped segment of resilient material such as plastic is provided. The illustrated clip member 170 has a pair of generally parallel leg segments 172 joined by a connecting bridge segment 174 having suitable elasticity and plasticity such that the clip member 170 exerts pressure from opposing directions sufficient to deform the valve 36 and maintain the valve 36 in the open position when the clip member 170 is selectively engaged on the valve member 36 as shown in FIG. 48, but permit the valve member 36 to return to the undeformed and closed configuration when the clip member 170 is selectively disengaged from the valve body 36 as shown in FIG. 47. Each leg segment 172 of the clip member 170 may include a generally convex inner surface adapted to apply pressure to the opposing sides of the valve body 36 when the valve body 36 is slidably inserted and received between the leg segments 172, the inner surfaces being spaced apart a distance determined to be equal to the distance required to the desired deformation of the valve body 36, taking into account the flexure of the leg segments 172 and bridge segment 174 due to the pressure exerted by the deformed valve body 36, the inner surfaces being spaced apart a certain distance from the bridge member 174 accounting for the oval or ovoid shape of the deformed valve body 36 such that complete engagement and maximal deformation is achieved when the valve body 36 contacts the bridge segment 174 as shown in FIG. 48. The ends of each leg segment 172 are preferably rounded or radiuses, and flare or taper outwardly relative to one another such that a distance c generally equal to or slightly greater than the undeformed diameter of the valve body 36 is provided between the inner surfaces of the leg segments 172 at the ends thereof to permit easy passage of the valve body 36 between the ends of the leg segments 172 as the clip member 170 is being selectively mounted engaged with the valve body 36.

Figure 50:
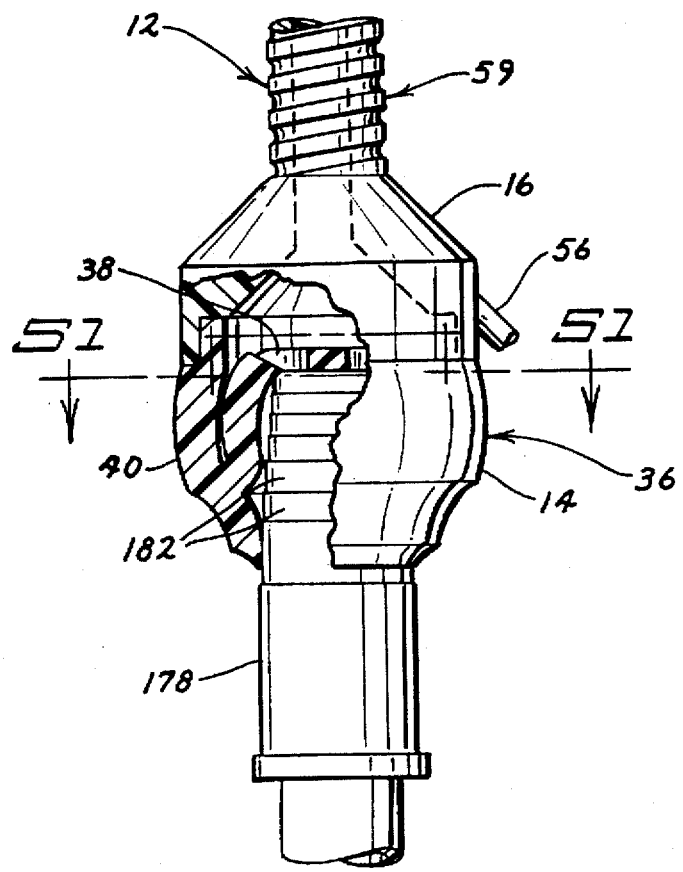
FIG. 50 is a partially broken away side view of a catheter connector inserted into and engaged within the distal opening of an alternate valve body of the present invention having essentially the same functional characteristics and elements so the valve body shown in FIGS. 1 and 3, wherein the catheter connector holds the valve element in an open configuration further illustrated in FIG. 51.

Referring now to FIGS. 50 and 51, it will be appreciated that the discharge opening 32 at the distal end 30 of the catheter body 12 and the truncated conical segment 42 of the valve wall 40 which define the proximal end 28 of the catheter body 12 are sufficiently pliable and resilient so as to be deformed or stretched to permit the insertion of the conventional Foley-type connector 178 having a drainage tube 180 attached thereto, insertion of such a connection 178 stretching the valve body 36 and deforming the valve member 38 to the open configuration permitting continuous voiding. A connector 178 having a plurality of generally cylindrical outer surfaces 182 of progressively increasing diameter as shown in FIG. 50 is a representative example of such a connector 178, but a connector 178 having a different type of tapered end will also perform suitably. One alternate connector 178 (not shown) includes a multiplicity of generally cylindrical outer surfaces 182 of progressively increasing diameter in which both the change in diameter and the height of each step are generally equal and relatively small, such that in overview the tip of the connector 178 appears to have a generally uniform taper on the order of 30°–60° but is actually composed of a multiplicity of steps or tiers. While it will be appreciated that any sufficiently rigid connector 178 having a diameter greater than the minimum relaxed diameter and less than the maximum stretched diameter of the discharge opening 32 will permit the connector 178 to be inserted into the distal end 30 of the catheter body 12 and engaged therein, the practical use of such an embodiment with connectors 178 already mounted on existing drainage tubes (not shown) will depend upon the elasticity of the material from which the distal end 30 of the catheter body 12 is fabricated, the frictional coefficient between that material and the connector 178, the diameter of the particular connector 178, and the maximum force normally expected to be exerted on the drainage tube. The connector 178 and drainage tube may be quickly disconnected from the distal opening 30 of the catheter 10 by manually applying manual tension or twisting force, and if the connector 178 becomes unintentionally dislodged from the distal end 30 of the catheter body 12 the valve 36 will automatically return to the undeformed and closed configuration.

Referring now specifically to FIGS. 43A, 43B and 44, where a preferred embodiment of the catheter body 12 is shown. A preferred catheter 10 of the present invention will combine the features of the illustrated catheter body 12 shown in FIG. 44 with the remaining features illustrated in FIG. 1. The illustrated catheter body 12 is preferably made of silicone rubber in a molding process like that discussed above in relation to the use of the mold 146 shown in FIGS. 41A and 41B. The catheter body 12 shown in FIG. 43A and 43B is preferably made in a mold (not shown) which is like the mold 146 of FIGS. 41A and 41B, except that the interior segments 154 and 156 of mold 146 have become part of the left and right mold parts 148 and 150, respectively, and there is no provision for creating an integrally molded inflation balloon 18. Instead, a sleeve 21, preferably made of silicone rubber, is provided to make an inflation balloon 18 for the illustrated catheter body 12. In a most preferred embodiment, the sleeve is sized to fit into the seat region 50 at either end of side wall 26 proximate the inflation opening 54, such that the balloon 18 is flush with the remaining portions of the side wall 26. The illustrated catheter body 12 is preferably molded using 50 durometer silicone rubber. The materials use will be selected from well-known silicone polymers. After the illustrated catheter body 12 is cured and the portion of the preformed inflation tube 52 is removed so that the edge of the inflation opening 54 is flush with the side wall 26 in the general area of the seat regions 50, a rod (not shown) is inserted into the central lumen 22 and the catheter body 12 is stretched down over the rod so that the length of the catheter body is increased by approximately 10 to 20 percent and the circumference of the catheter body 12 is decreased. When the catheter body 12 is in this stretched configuration, the sleeve 21 slides easily over the catheter tip 28 and the ends of the sleeve 21 are positioned around the seat regions 50 proximate the inflation opening 54. The tension on the catheter body 12 is then relieved so that it returns to a normal configuration and an adhesive is inserted between the sleeve 21 and the side wall 26 in the area of each of the respective seat regions. In preferred embodiments the sleeve 21 is made of silicone rubber having a durometer of 20. The sleeve 21 is preferably cut to size from an elongated sleeve material made of silicone rubber having a durometer of 20 purchased from Specialty Silicone, Inc., Paso Robles, Calif. The adhesive is preferably a two-part medical grade silicone adhesive from Dow Chemical Co., Inc., Midland, Mich., such as Q74840 which is a silicone rubber room temperature vulcanizing (RTV) adhesive having a durometer of 40 when cured. The respective parts of this adhesive are mixed prior to usage and injected between the sleeve 21 and the side wall 26 at both ends of the sleeve 21 proximate the respective seat regions 50, preferably using a 20 gage nozzle (not shown). As the nozzle is inserted between the sleeve 21 and the side wall 26 at one end of the sleeve 21 or the other, and pressure, preferably about 35 psi, is applied to the mixed two-part adhesive, the catheter body 12 is rotated so that the adhesive is applied circumferentially about the side wall 26 after the adhesive is applied, the catheter body 12 is placed in an oven at about 350° F. for about 5–10 minutes to effect a cure of about 80 percent. The catheter body 12 is then set aside and cooled, and the cure is completed. Subsequently, the valve 36 is added by sealing the valve 36 to the proximal portion 16 of the catheter body 12 using a similar adhesive in a similar manner, and the fully-formed catheter is set aside to cure and is subsequently tested, packaged, sterilized and shipped.

The preferred valve member 38 has three curved valve openings 76. The respective edges of valve openings 76 define three intermediate ribs 78 connected to one another in a central location to form a Y-shape and separating three valve segments 80 from one another. When the valve wall 40 is squeezed radially inward from any two diametrically opposing sides, such as shown by the hollow arrows in FIG. 5, the valve wall 40 and valve member 38 are deformed substantially from the closed configuration shown in FIGS. 3 and 4 to an open configuration as shown in FIG. 5. At least one element 80 of the arcuate dome 38 flexes proximally or upstream, and the boundaries of the valve openings 76 defined by the contacting surfaces between the valve segments 80 and intermediate ribs 78 separate to create one or more openings through which fluid may flow from the interior of the valve 36 and the central lumen 22 to the discharge opening 32. When the radially inward pressure is released, the valve 36 returns to the closed configuration shown in FIGS. 3 and 4, with the edges or contact surfaces of the valve segments 80 contacting the closely conforming surfaces of the intermediate ribs 78 to maintain proper alignment and closure of the valve openings 76 without the valve segments 80 overlapping or being axially displaced from the intermediate ribs 78 so as to present a gap through which fluid can drain.

The cuts or slits through the valve member 38 forming the valve openings 76 extend from the highest respective point on the apex 66 of the valve member arcuate 38 downwardly or distally and intersect with a portion of the peripheral edge 74 which demarks the lowest or most distal point upon the convex surface 70. These intersection points 82 between the valve openings 76 and the peripheral edge 74 of the dome are disposed at or near the radial center of trough 75 in the intermediate region 68 at approximately the lowest or most distal point, with the entire upstream surface of the valve member 38 being disposed more proximal than those intersection points 82, thereby ensuring that when the valve openings 76 are in the open configuration the valve member 38 will not present any concave recesses disposed more proximal to the intersection points 82, and fluid within the interior of the valve 36 will drain completely through the valve openings 76 even though there is little or substantially no remaining fluid pressure.

It may be appreciated that a variety of surface configurations and non-uniform terrains may be utilized for the convex surface 70 and concave surface 72 of the valve member 38. However it is preferred that in any such configuration no portion of the upstream face of the trough 75 along the shortest path from an intersection point between the valve opening 76 and the peripheral edge 74 and the adjacent or most proximate portion of the valve wall 40 be disposed further downstream than that intersection point, thereby preventing an aliquot of fluid from being trapped in a recess or cavity rather than draining through the valve opening due to the force of gravity when the valve member 38 is deformed and the valve 36 is maintained in the open position. In this preferred embodiment, that arcuate segment or dome of the valve member 38 defines a generally uniform ovoid section extending downwardly to the peripheral edge 74, with the peripheral edge 74 defining a plane oriented generally perpendicular to the longitudinal axis 34 of the catheter body 12 within the interior region of the valve 36.

In addition, the slits defining the valve openings 76 may extend from the arcuate dome 38 across the peripheral edge 74 toward the interior surface of the side wall 40, but preferably not actually contacting or intersecting the interior surface of the side wall 40. In this manner, the width of the valve opening 76 is increased in the region directly adjacent to or surrounding the intersection points 82 between the valve openings 76 and the peripheral edge 74 (representing the bottom-most point of the trough 75) compared with the width of a conventional valve opening 76 at the intersection with the side wall 40 of the valve 36. The result is to increase low-pressure drainage compared with conventional dome-type valves, and minimize the risk that the side wall 40 will be damaged during fabrication of the valve openings 76. This also increases the eventual maximum width of the valve openings 76 at the greatest distances from the side wall 40 when the dome 38 is fully deformed. Given a predetermined separation between the peripheral edge 74 of the valve member 38 and the side wall 40, the valve opening 76 could extend from the valve member 38 past the intersection points 82 a distance on the order of one half that separation.

Figure 16:
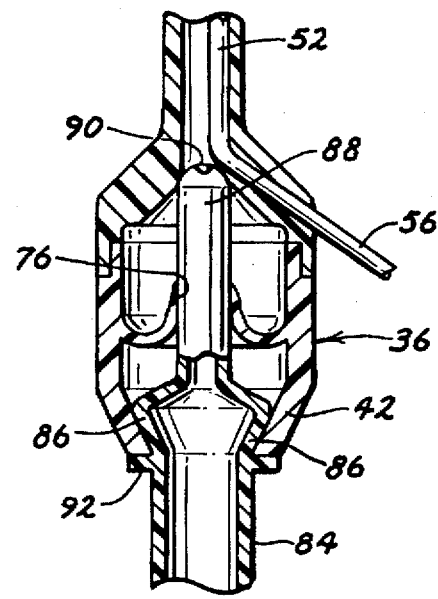
FIG. 16 is a cross-sectional view of the lower portion of the catheter body of FIG. 1 with a drainage tube connecter inserted through the valve element.

The particular configuration of the valve member 38 shown in FIGS. 1 and 3–5 permits use of the catheter 10 with a drainage tube connector 84 as shown particularly in FIG. 16. The drainage tube connector 84 includes a tapered neck 86 sized and shaped to fit and engage within the truncated conical segment 42 of the valve 36 and thereby be retained against axial movement or inadvertent disconnection. The proximal end of the tapered neck 86 has a generally hollow stent tube 88 that radially displaces the intermediate ribs 78 as the stent tube 88 is inserted through the valve member 38, and extends proximally through one of the valve openings 76 and into the distal end of the central lumen 22. The proximal end of the stent tube 88 preferably engages the side wall 26 of the central lumen 22, disposing an aperture 90 in fluid communication with the central lumen 22. This frictional engagement resists inadvertent or unintentional disconnection of the drainage tube connector 84 from the valve 36, and further ensures that fluid does not leak around the periphery of the stent tube 88 into the interior of the valve 36. The valve elements 80 and intermediate ribs 78 return to the closed and sealed position when the stent tube 88 is removed along with disconnection of the drainage tube connector 84. A radial shoulder 92 on the drainage tube connector 84 prevents overinsertion of the stent tube 88.

Figure 9:
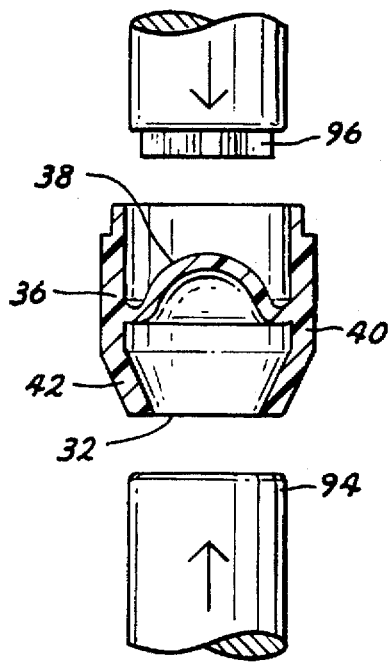
FIG. 9 is a diagrammatic cross-sectional view of the valve of FIG. 3 with a mandril and a cutting tool displaced therefrom.
Figure 10:
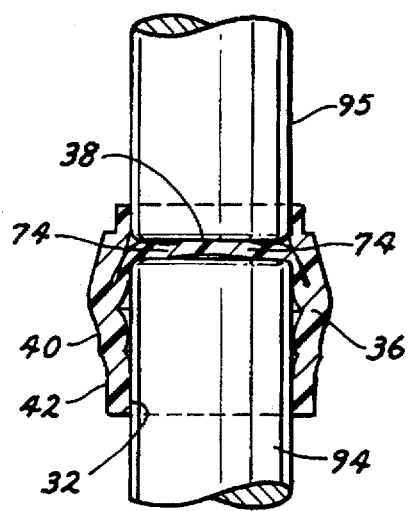
FIG. 10 is a diagrammatic cross-sectional view of the valve of FIG. 3 with the mandril and cutting tool disposed within the interior of the valve and the valve element deformed.

Referring now particularly to FIGS. 9 and 10, it will be appreciated that the valve openings 76 are cut through the valve member 38 by inserting a radially oversized mandril 94 through the discharge opening 32 of the valve 36, thereby flexing the truncated conical segment 42 outward and stretching the valve wall 40 and valve member 38 radially outward and away from the longitudinal axis until the valve member 38 is in a generally planar or flat configuration as shown in FIG. 10. A cutting tool 95 having a blade member 96 on its leading edge is inserted through the proximal opening in the distal portion 14 of the valve 36, and into close proximity to the valve member 38. Using opposing pressure exerted by the mandril 94 to restrain the valve member 38 against axial movement, the blade member 96 is forcibly pressed toward the mandril 94 so that the blade member 96 contacts and completely penetrates the valve member 38 and defines the particular pattern or configuration of valve openings 76 that is desired. The top surface of the mandril 94 is fabricated from a sufficiently compliant material such that the blade member 96 may score the surface of the mandril 94 to ensure complete penetration of the valve member 38. The cutting tool 96 and mandril 94 are removed from the interior of the valve 36, which is released from the stretched position so that the valve member 38 returns to its normally un deformed convoluted configuration as shown in FIG. 9. The truncated conical section 42 of the valve 36 may initially be stretched to permit ingress of the mandril 96 using a plurality of fingers (not shown) or other segments that are inserted within the valve 36 through the distal opening 32 and are separated to stretch the valve 36 sufficiently to permit passage of the mandril 94. The fingers or other segments may be removed during the cutting operation to maintain uniform radial tension o the valve member 38. It may further be noted in FIG. 10 that in the deformed configuration, the valve member 38 may be stretched across the top and down the sides of the mandril 94, with the generally flat or planar section corresponding to the area of the valve member 38 within and defined by the peripheral edge 74 and encompassing the portion of the intermediate section 68 or the trough 75 disposed within the peripheral edge 74. In an embodiment where the valve openings 76 cross the peripheral edge 74 and extend beyond the lowest point of the trough 75, the mandril 94 must be slightly larger than the diameter of the peripheral edge 74. It may be appreciated that the valve member 38 may not achieve a completely flat or planar configuration, since tension decreases proportionately to the proximity to the center point or longitudinal axis 34 of the valve member 38, however the blade member 96 presses the valve member 38 substantially flat prior to cutting.

Figure 11:
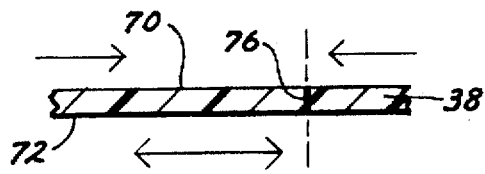
FIG. 11 is a diagrammatic cross-sectional view of a segment of the valve element of FIG. 10 in the deformed configuration showing a cut.
Figure 13:
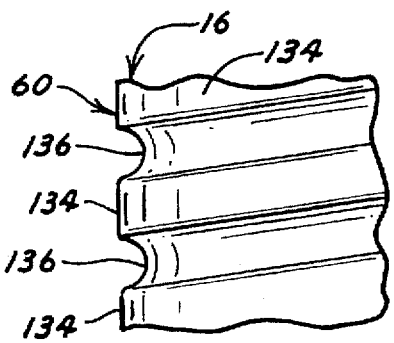
FIG. 13 is an enlarged detailed view of the lands and grooves of the helical threading of the catheter body of FIG. 1.
Figure 12:
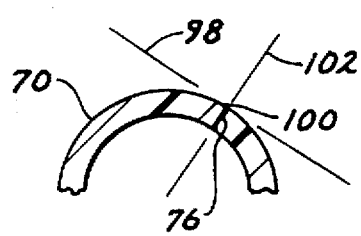
FIG. 12 is a diagrammatic cross-sectional view of a segment of the valve element of FIG. 10 in the relaxed configuration showing the cut.

Referring now also to FIGS. 11 and 12, the process of deforming the valve member 38 to a generally planar configuration produces compressive forces along the normally convex surface 70, and tensile forces along the normally concave surface 72. These forces are represented by the force arrows shown in FIG. 11. When the valve member 38 is cut perpendicularly in the deformed configuration as shown in FIGS. 10 and 11 and then released to the unstressed and convoluted configuration as shown in FIG. 12, the cut forming the valve opening 76 has two confronting and contacting faces. The shortest straight line path for these faces is defined by a line 102 generally perpendicular to and bisecting a plane 98 disposed tangentially to the intersection point 100 of the convex surface 70 and the cut forming the valve opening 76. Due to the compressive and tensile forces and the density and malleability of the material from which the valve member 38 is fabricated, the cut forming the valve opening 76 may traverse a slightly curved or arcuate path rather than a straight line path, and the angle of the cut line 76 relative to the normal line 102 may also vary slightly as the path of the valve opening 76 is traversed from one end to the other. If the cut forming the valve opening 76 is oriented at an angle relative to the normal line 102, the cut will have an effective depth greater than the normal thickness of the valve member 38, thereby increasing the contact area between the confronting faces of the valve segments 80 (or valve segment 80 and intermediate rib 78) compared with the cut extending through the valve member 38 normal or perpendicular to its surfaces 70, 72 along line 102.

In the three-element valve 36 with intermediate ribs 78 shown in FIGS. 4 and 5, the top valve member 38 deforms upwardly and is displaced a greater radial and axial distance than the intermediate ribs 78 or lower two valve elements 80. When pressure is released, the intermediate ribs 78 and lower two valve elements 80 return to their original closed configuration prior to the top valve element 80, which subsequently nests and seats properly against the intermediate ribs 78 as the valve element 80 moves radially and axially back into contact with the intermediate ribs 78.

Figure 7:
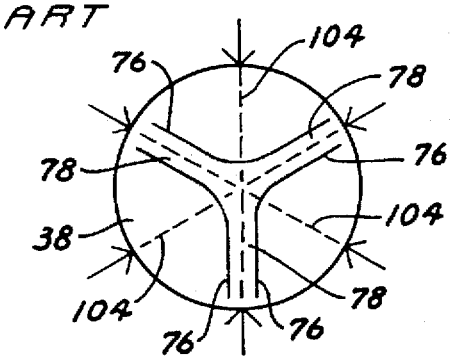
FIG. 7 is a diagrammatic top plan view of a preferred embodiment of the dome-type valve of the present invention similar to that shown i FIG. 4 having three equilateral valve elements and three centrally connected intermediate ribs forming a Y-shape.

Referring now also to FIGS. 4, 5, and 7, it will be appreciated that pressure applied to opposing sides of the valve 36 as shown in FIG. 5 may be oriented along any on of three equilaterally spaced diametric axes 104 to open one of valve elements 80 substantially upward and shift the remaining valve elements 80 and central connection of the intermediate ribs 78 slightly upward and radially in the opposite direction away from the valve element 80 that opens upward. Conversely, pressure applied from opposing sides but disposed between two of the axes 104 will partially deform a pair of valve elements 80 and valve openings 76 proportionately to the angular separation between the adjacent axes 104 and the source of pressure, thereby providing approximately the same total flow area.

Figure 6:
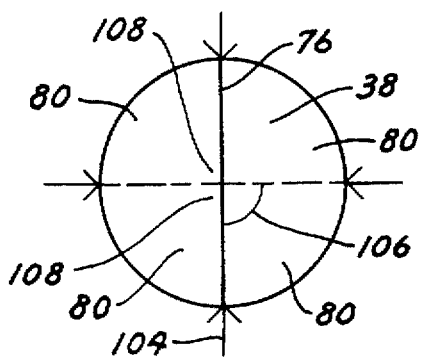
FIG. 6 is a diagrammatic top plan view of a dome-type valve having a first straight slit and a second straight slit in phantom oriented perpendicular to the first straight slit.
Figure 8:
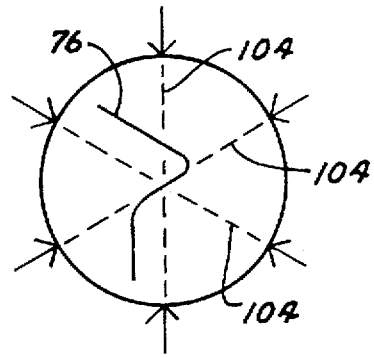
FIG. 8 is a diagrammatic top plan view of an alternate embodiment of the dome-type valve having a serpentine slit.

Referring to FIGS. 6–8, it may be appreciated that the selection of a preferred configuration for the valve openings 76 or slits and the valve elements 80 in a dome-type valve 36 depends upon balancing several factors, the hardness, curvature, and thickness of the material at various locations on the valve element 80 (affecting the "memory" of the valve element 80 and the force, speed, and consistency with which it returns to the original closed position), the relative length and width of the valve element 80, the number of the valve elements 80, and their respective orientation along contact or seating surfaces.

Referring now to FIG. 6, a single slit or valve opening 76 placed along the diameter of the valve member 38 produces a pair of valve elements 80 and a single axes 104. This valve configuration has been referred to herein as a uniaxial valve 36, since pressure must be applied at two opposing surfaces in a set orientation, such as with a "duckbill" valve. Adding a second slit (shown in phantom in FIG. 6) perpendicular to the first valve opening 76 that intersects as a single passage. The number of axes 104 increases to two, but the angle 106 between the adjacent edges of the valve elements 80 along the valve openings 76 decreases to approximately 90° thereby diminishing the memory of the valve elements 80 at the points 108 and increasing the likelihood that the valve elements 80 will overlap or not seat properly when the valve 36 closes.

Figure 21:
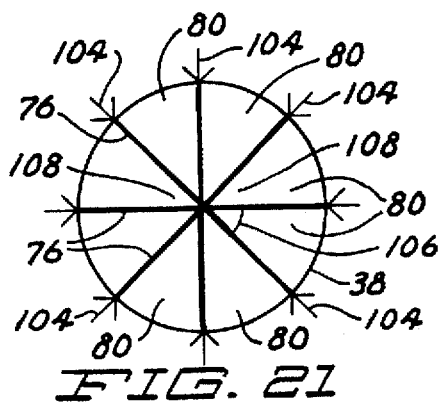
FIG. 21 is a diagrammatic view of a dome-type valve having four diagonal slits and eight valve elements.
Figure 22:
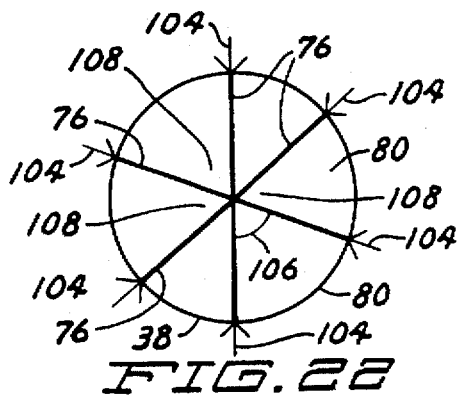
FIG. 22 is a diagrammatic view of a dome-type valve having three diagonal slits and six valve elements.

Increasing the number of diametric slits to four as shown in FIG. 21 increases the corresponding number of valve openings 76 and valve elements 80 to eight, as well as the number of axes 104 to four, but decreases the angle 106° to 45° and produces a very significant decline in the memory of the valve elements 80 adjacent to the points 108 relative to the configuration shown in FIG. 20. This results in a valve than can easily be deformed and provides good multiaxial characteristics, but closes slowly or incompletely, and allows the valve elements 80 to "catch" and overlap one another adjacent the points 1108 so that the valve 36 is likely to leak significantly. Decreasing the number of diametric slits to three as shown in FIG. 22 decreases the corresponding number of valve openings 76 and valve elements 80 to six, as well as the number of axes 104 to three, but increases the angle 106° to 60° and increases the memory characteristics of the valve elements 80 adjacent to the points 108.

Figure 23:
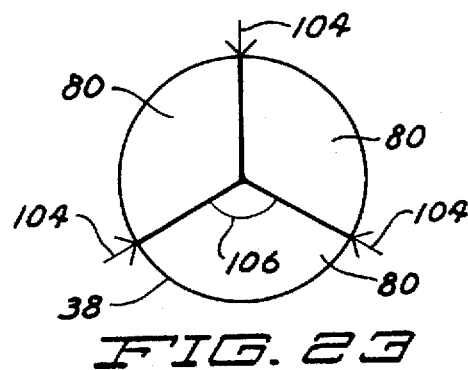
FIG. 23 is a diagrammatic view of a dome-type valve having three equilateral slits that intersect at a central point and form three valve elements.

One alternative is to provide a valve 36 with valve openings that do not cross the valve member 38 diametrically, as shown in FIG. 23. For example, a valve member 38 defining three radial slits joined at the center point produces three valve openings 76 and three equilateral-spaced axes 104, with an angle 106° of 120° formed at the points 108. Continuing the progression suggests that the lower number of slits and valve elements 80 the greater the angle 106 at the points 108 and the better the memory characteristics. However, the final step results in a valve 36 with a single slit forming one valve opening 76 with no points 108, but with uniaxial orientation along a single axis 104 as shown in FIG. 6.

Figure 24:
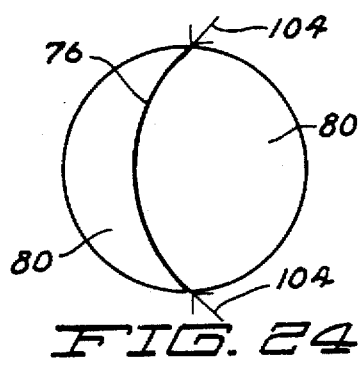
FIG. 24 is a diagrammatic view of a dome-type valve having one curved slit intersecting the diameter of the valve at the ends thereof to form two valve elements.

However, it may also be appreciated that the effective number of axes 104 defined by a valve 36 having a single slit and one valve opening 76 may be increased by curving the slit or valve opening 76 as shown in FIG. 24. Pressure applied to opposing surfaces of the valve will open the portion of the valve opening 76 which extends generally parallel with the axes 104 connecting the two pressure points. Stated conversely, segments of the slit or valve opening 76 define lines or axes 104, and pressure applied to opposing points along a line parallel to these axes 104 will cause that segment of the valve opening 76 to open.

Figure 35:
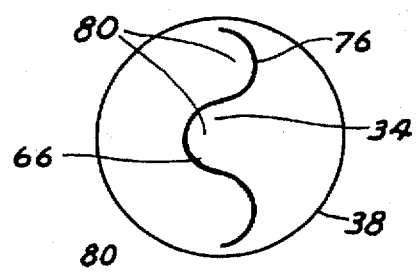
FIG. 35 is a diagrammatic view of a dome-type valve having one serpentine slit defining three curves of generally equal radii, with one central curve overlapping the center point of the valve.

It may be appreciated that a valve 36 having multiple axes 104 may be fabricated using a single continuous slit or valve opening 76 if that slit or valve opening 76 traverses a "serpentine" pathway as shown in FIGS. 8 and 35, with discrete segments of the valve opening 76 being orientated generally parallel with the axes 104 along which pressure is applied from opposing sides of the valve 36. The "true" number of axes 104 is actually defined by the number of discrete segments of the valve opening 76 that are oriented at divergent angles and together form a composite serpentine curve, however for purposes of simplicity the axes 104 aligned with the various curved segments of the valve opening 76 have been discounted. As such, the axes 104 indicated become the "major" or "primary" axes 104 responsible for deforming and opening a significant portion of the valve member 38 in normal operation. Orientation of these "primary" axes 104 at three equilateral positions produces a suitable multiaxial valve 36 for the application described herein. It is understood that curved slits or valve openings 76 such as those shown in FIGS. 4, 7, and 24–33 may also be considered "serpentine" in the sense that they traverse arcuate paths and present a multiplicity of axes each parallel to a segment of the slit, with the axes 104 parallel to the ends of the slits usually constituting the major or primary axes 104.

Figure 25:
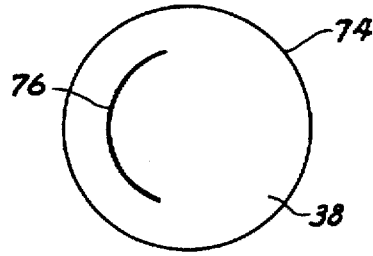
FIG. 25 is a diagrammatic view of a dome-type valve having one curved slit that does not intersect the diameter of the valve at the ends thereof and forms two valve elements.
Figure 26:
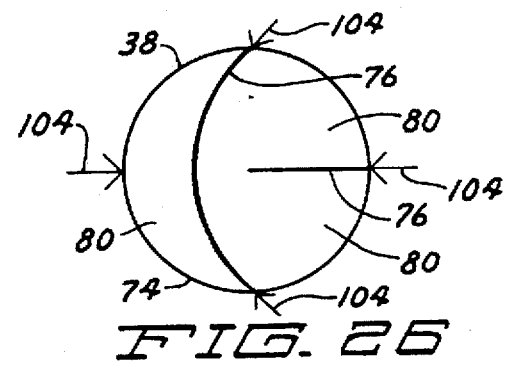
FIG. 26 is a diagrammatic view of a dome-type valve having one curved slit that intersects the diameter of the valve at the ends thereof and a straight slit that does not intersect the curved slit and forms three valve elements.
Figure 27:
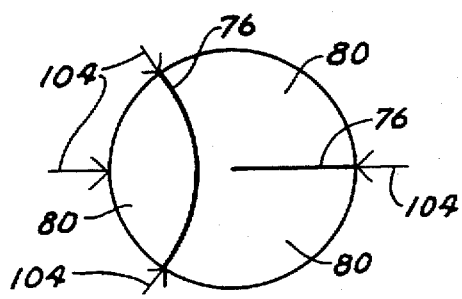
FIG. 27 is a diagrammatic view of a dome-type valve similar to that shown in FIG. 26, but with the orientation of the curved slit reversed.
Figure 28:
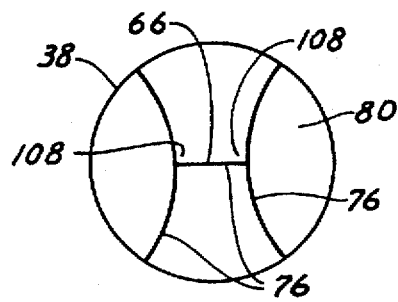
FIG. 28 is a diagrammatic view of a dome-type valve having two curved slits that are connected at their midpoints by a straight slit to form four valve elements.
Figure 29:
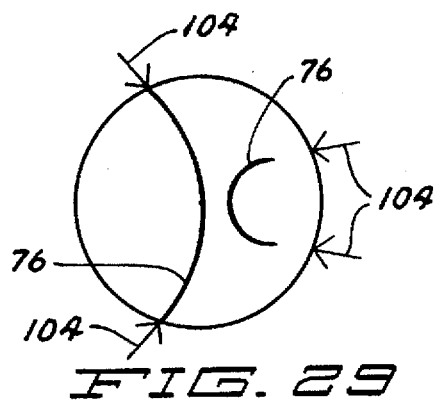
FIG. 29 is a diagrammatic view of a dome-type valve having two curved slits of differing radii that do not intersect.
Figure 30:
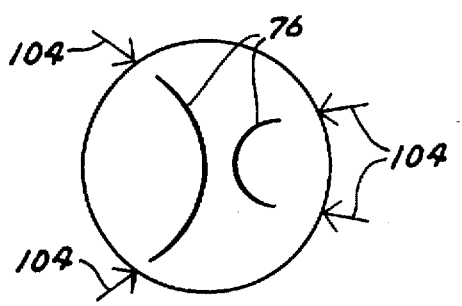
FIG. 30 is a diagrammatic view of a dome-type valve having two curved slits of differing radii which do not intersect each other as in FIG. 29, but one of which intersecting the peripheral edge.
Figure 31:
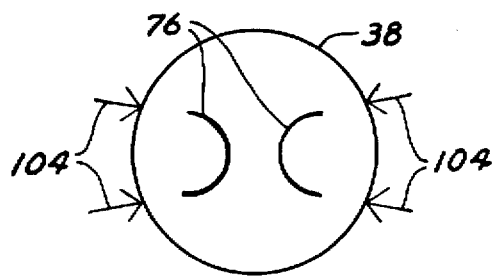
FIG. 31 is a diagrammatic view of a dome-type valve having two curved slits generally equal radii that convexly confront and are spaced apart from one another.
Figure 33:
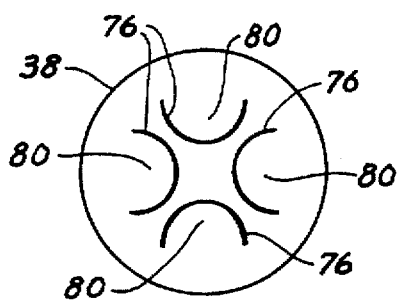
FIG. 33 is a diagrammatic view of a dome-type valve having four curved slits of generally equal radii that convexly confront and are equidistantly spaced apart from one another.
Figure 34:
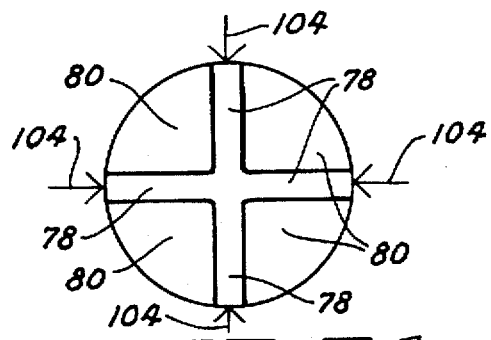
FIG. 34 is a diagrammatic view of a dome-type valve having four curved slits that convexly confront one another to form four valve elements separated by four intermediate ribs that intersect and are joined in a central region.

It may be readily appreciated that the configurations of dome-type valves 36 is described herein may be categorized into three groups: straight-slit valve openings 76 (as shown in FIGS. 6 and 21-23; valve openings 76 defining intermediate ribs 78 (as shown in FIGS. 4, 5 and 7); and serpentine valve openings 76 (as shown in FIGS. 8 and 24). However, the variety and complexity in the combinations of these valve openings 76 can increase. For example, FIG. 25 shows a single valve opening 76 comprising a single radially-offset curved slit that does not intersect the peripheral edge 74 of the valve member 38. FIG. 26 shows a curved slit defining a first curved valve opening 76 intersecting the peripheral edge of the valve member 38, and a straight slit defining a second valve opening 76 having an axis 104 oriented acutely to both axes 104 of the curved valve opening 76. This configuration may be considered to produce two valve openings 76 with three valve elements 80. In FIG. 27, the orientation of the curved valve opening has been reversed so that the ends of the valve opening 76 do not intersect diametrically opposed points on the peripheral edge 74 of the valve member 38. FIG. 28 includes two curved valve openings 76 connected at their center points by a straight valve opening 76 that bisects the apex 66 of the valve member 38, thereby forming four valve elements 80 having centrally located points 108. FIGS. 29 and 30 shown two potential orientations of a valve 36 having two curved valve openings 76 each of different radii, and increasing the number of available axes 104. FIGS. 31-33 show three potential configurations for equidistantly-spaced curved valve openings 76 of approximately equal radii. It may be appreciated that the configuration shown in FIG. 32 approaches the configuration of the valve 36 shown in FIGS. 4 and 7, having three valve elements 80, three valve openings 76, and three intermediate ribs 78. Similarly, the configuration shown in FIG. 33 approaches the configuration of the valve 36 shown in FIG. 34, having four valve elements 80, four valve openings 76, and four intermediate ribs 78. While the valve 36 shown in FIG. 33 would effectively have three primary axes 104 spaced equidistantly or equilateral, the valve 36 shown in FIG. 34 has only two perpendicular axes 104. Finally, a configuration for a serpentine valve 36 is shown in FIG. 35 that provides two or three valve elements 80 using a single valve opening 76, depending upon how one differentiates the two adjacent valve elements 80 on the left-hand side of the FIG. 35, and wherein the center valve element 80 overlaps or encompasses the apex 66 and longitudinal axis 34 of the valve member 38, thereby providing a section of the valve member 38 that may be easily displaced by insertion of the stent tube 88 of a drainage tube connector 84.

The use of curved slits and intermediate ribs 78 produces a synergistic effect by providing a multiaxial valve 36 that will seat reliably and completely, and eliminating sharp corners that can overlap or catch due to poor memory in the adjacent portions of the valve elements 80.

It should be noted that the preferred valve 36 has been described herein as having a dome-type valve member 38, however this representative terminology can include a variety of other types of valve members 38 having corresponding shapes such as conical, truncated conical, oval or ovoid, pyramidal, trapezoidal. The common element among these configurations of valves 36 is their inclusion of an elevated region disposed more proximally and forming an apex 66, and a surrounding lower portion disposed more distally and forming a base or peripheral edge 74 which may gradually and uniformly transition into a trough 75.

While the preferred embodiments of the urinary catheters 10 and methods of use and methods for manufacture the same as currently contemplated have been described in detail with reference to the attached drawings it is understood that various changes and adaptations may be made in the urinary catheters 10 of the present invention and elements thereof, and to the elements of the inventive methods of use and manufacture described herein without departing from the spirit and scope of the appended claims.

What is claimed is:

1. In an indwelling urinary catheter for use by a patient to manage urinary incontinence or retention, the patient having a bladder communicating with a urethra, the urethra having a distal end portion including a rim of a urethral orifice surrounded by a surface area proximate the urethral orifice, the catheter having a catheter body defining both an exterior surface and a central lumen through which the urine can flow from the bladder when the catheter is inserted at least partially into the bladder and the urethra, and a discharge valve in fluid communication with the central lumen, the discharge valve having a valve body including a valve wall defining an interior region and an inner surface, the discharge valve further including a valve membrane having an upper surface and a lower surface, the valve membrane having a plurality of valve openings, each of the plurality of valve openings having both a closed and an open position, wherein the patient can selectively manipulate the valve such that at least one of said plurality of valve openings can (1) be opened from a closed position to allow urine to pass through the valve from the bladder and the central lumen, and (2) be closed from an open position to retain urine in the bladder and the central lumen, the valve membrane having a generally circular shape interconnected at its periphery to the interior surface of the valve wall, the improvement comprising:

the valve membrane being dome-shaped in a convex center portion and having a trough encircling the convex center portion, wherein the upper surface of the valve membrane proximate the trough is further distally removed from proximal portions of the catheter body than the upper surface proximate the convex center portion, each of said plurality of valve openings being an elongated slit in the valve membrane which passes through both the upper and lower surfaces of the valve membrane;

at least one of said plurality of valve openings having an arcuate shape, wherein the elongated slit passes from a first location proximate the trough on the upper surface, to a second location closer to an apex of the convex center portion relative to the first location, and then to a third location more removed from the apex of the convex center portion as compared to the second location, wherein the valve is multiaxial such that at least one of said plurality of valve openings can be manipulated by a patient from a closed position to an open position when the patient compresses opposite sides of the valve wall together when engaging the valve wall in a plurality of different locations on the outer surface of the valve wall.

2. The indwelling urinary catheter of claim 1 wherein there are at least two valve openings having an arcuate shape and the elongated slit passes from said first location, to said second location, to said third location.

3. The indwelling urinary catheter of claim 1 wherein the catheter has an inflation lumen and an inflatable retention balloon, said retention balloon being axially symmetrical with respect to the catheter body.

4. The indwelling urinary catheter of claim 1 wherein the catheter body has a threaded area on its exterior surface and a retention collar engaged around the catheter body proximate the threaded area, the threaded area providing helical threading disposed along a portion of the exterior surface of the catheter body, the retention collar having mated threading disposed within a bore of the collar such that the collar can be mounted on the catheter body in threaded engagement therewith.

5. The indwelling urinary catheter of claim 1 wherein the hardness of the catheter and elements thereof, as measured by durometer measurements, differs in that the balloon has a lower durometer than other portions of the catheter.

6. The indwelling urinary catheter of claim 1 wherein the discharge valve has a discharge opening at the distal end of the valve and a drainage tube connector can be inserted into and engaged within the discharge opening such that the connector engages the lower surface of the valve membrane so that the membrane is deformed and the valve membrane can be deformed such that the valve openings remain in an open position when the valve membrane is so engaged.

7. In a catheter for use by a patient to control urinary incontinence or retention, said patient having a bladder and a urethra, said urethra having a distal end, said catheter including a catheter body to be disposed at least partially within said urethra of said patient, said catheter body defining a lumen through which urine flows from said bladder to said distal end of said urethra, a valve connected to said catheter body in fluid communication with said lumen such that said patient selectively manipulates said valve between a closed position and an open position to void urine from said bladder through said lumen, said valve including a valve body having a valve wall defining an interior region and an inner surface, and a valve member connected to said valve wall and disposed within said interior region, the improvement comprising:

the valve member having a generally arcuate segment defining a generally convex surface, a generally concave surface, and a peripheral edge, said convex surface of said valve member being oriented facing generally upstream opposing the flow of urine through the valve body, the valve member further defining a first valve opening and a second valve opening each extending entirely therethrough and disposed in fluid communication with the lumen, the valve member being generally deformable when the patient selectively manipulates the valve so as to permit the flow of urine through said first valve opening or said second valve opening or both, the valve member including a first segment, a second segment, and a rib member, at least a portion of said rib member being disposed between and contacting both said first segment and said second segment of said valve member when the valve is closed, said first segment or said second segment or both being displaced a distance apart from said rib member when said valve member is deformed.

8. The catheter of claim 7 wherein the first segment, the second segment, and the rib member of the arcuate segment of the valve member are integral with one another.

9. The catheter of claim 7 wherein the first segment, the second segment, and the rib member of the arcuate segment of the valve member are formed integrally with one another.

10. The catheter of claim 7 wherein the first valve opening and the second valve opening are separated from and do not intersect one another, and wherein the first segment, the second segment, and the rib member of the arcuate segment of the valve member are a fabricated as one piece.

11. The catheter of claim 7 wherein the first segment of the valve member defines a first surface contacting the rib member when the valve is in the closed position, and the second segment of the valve member defines a second surface contacting the rib member when the valve is in the closed position, said first surface of the first segment and said second surface of the second segment not contacting one another when the valve is in the closed position.

12. The catheter of claim 7 wherein the first valve opening does not intersect the second valve opening.

13. The catheter of claim 7 wherein the valve member defines a third segment and a third valve opening, at least a second portion of the rib member being disposed between and contacting both the first segment and said third segment of the valve member when the valve is closed, at least a third portion of the rib member being disposed between and contacting both the second segment and said third segment of the valve member when the valve is closed.

14. The catheter of claim 13 wherein the third segment of the valve member defines a third surface contacting the rib member when the valve is in the closed position, said third surface of the third segment not contacting either the first surface of the first element or the second surface of the second element when the valve is in the closed position.

15. The catheter of claim 13 wherein the third valve opening does not intersect either the first valve opening or the second valve opening.

16. In a catheter assembly for use by a female patient to manage urinary incontinence or retention, said patient having a bladder and a urethra, said bladder having an inner wall and said urethra having a distal end and a surface area surrounding the distal end, said catheter including a catheter body which is disposed at least partially within the urethra when the catheter assembly is in use by the patient, the catheter body defining an exterior surface and a central lumen extending from the bladder to the distal end of the urethra when in use by the patient and an inflatable balloon interconnected with the catheter body and disposed at least partially within the bladder during use so as to retain the catheter body within the urethra and minimize intra-urethral leakage of urine out of the bladder along the exterior surface of the catheter body and through the urethra, a collar disposed on the catheter body generally proximate to the distal end of the urethra, the collar having a bore, the improvement comprising:

helical threading disposed along a portion of the exterior of the catheter body and mating threading disposed within the bore of the collar, such that the collar is mounted in threaded engagement on the catheter body and rotation of the collar relative to the catheter body in an angular direction of rotation moves the collar axially a distance generally proportionate to the rotation of the collar relative to the catheter body, said axial direction determined by said angular direction of rotation, wherein the collar can be used to create a tension on the catheter body and the inflatable balloon by tightening the collar up against the surface area surrounding the distal end of the urethra when the balloon is located in a predetermined position relative to the inner wall of the bladder, the tension biasing the balloon against the wall of the bladder to minimize intra-urethral leakage along said exterior surface of the catheter body.

17. The catheter assembly of claim 16 wherein the helical threading and the mating threading form a plurality of alternating lands and grooves having a plurality of land faces and a plurality of grooves, said plurality of land faces each being generally planar, wherein the longitudinal diameter of the catheter body is generally the same as the distance between two planes generally disposed against opposite sides of the catheter body proximate the helical threading.

18. The catheter assembly of claim 16 wherein a first portion of the catheter body can extend from within said urethra of the patient such that said first portion of the catheter body may be gripped while the collar is rotated to adjust the collar axially along the catheter body.

19. The catheter assembly of claim 16 wherein the retention collar has a concave upper surface.

20. The catheter assembly of claim 16 wherein the inflatable balloon is axially symmetrical.

21. The catheter assembly of claim 16 wherein the hardness of the catheter and elements thereof, as measured by durometer measurements, differs in that the balloon has a lower durometer than other portions of the catheter.

22. The catheter assembly of claim 16 wherein the catheter has a multiaxially discharge valve in communication with the central lumen, the discharge valve having a valve membrane a plurality of valve openings, wherein the discharge valve can be selectively manipulated to open at least one of the plurality of valve openings.

23. The catheter assembly of claim 16 wherein the discharge valve has a discharge opening at the distal end of the valve and a drainage tube connector can be inserted into and engaged within the discharge opening such that the connector engages the lower surface of the valve membrane so that the membrane is deformed and the valve openings are in an open position.

24. In a catheter for controlling urinary incontinence or retention in a patient having a bladder, said catheter having a valve which the patient can selectively manipulate from a closed position to an open position in order to discharge fluid from the bladder, said valve oriented to normally oppose a flow of the fluid from an upstream direction when said valve is in a closed position, the improvement comprising:

a valve body, said valve body having a valve wall defining an interior and a distal opening; and a valve member, said valve member extending from and being connected to said valve wall at a junction and defining a valve opening extending therethrough, said valve member having the generally convex surface confronting the flow of the fluid from the upstream direction, and a peripheral trough generally surrounding the generally convex surface, the peripheral trough being generally radially concave and being disposed more closely proximate to said distal opening than said generally convex surface, whereby the valve opening intersects the peripheral trough to permit drainage of the fluid through the valve opening.

25. The catheter of claim 24 wherein the convex surface defines a peripheral edge, said peripheral edge being substantially coextensive with a most distal portion of the peripheral trough, and wherein the valve opening intersects said peripheral edge in at least one intersection point.

26. The catheter of claim 25 wherein the valve opening extends from the convex surface of the valve member, intersects the peripheral edge, and extends a distance from the convex surface past the intersection point toward the valve wall.

27. The catheter of claim 26 wherein the peripheral edge and the valve wall are spaced apart by a separation, and wherein the distance is on the order of one half said separation between the peripheral edge and the valve wall.

28. In a valve for controlling a flow of a fluid, said valve being selectively manipulated by a user from a closed position to an open position in order to permit the flow of said fluid, said valve oriented to normally oppose said flow of said fluid from an upstream direction to a downstream direction along a generally linear axis when said valve is in a closed position, the improvement comprising:

a valve body, said valve body having a valve wall defining an interior and a distal opening; and a valve member, said valve member extending from and being connected to said valve wall and defining a first valve opening and a second valve opening each extending therethrough, said valve member having a generally convex surface confronting the flow of the fluid from the upstream direction, the generally linear axis intersecting said valve member within said generally convex surface, said first valve opening defining a first pathway along said generally convex surface, said second valve opening defining a second pathway along said generally convex surface, said first pathway or said second pathway or both curving along said generally convex surface when viewed from and relative to a perspective along the generally linear axis, whereby the patient exerts pressure on the valve body to deform the valve member and move the valve member to an open position.

29. The valve of claim 28 wherein the first valve opening and the second valve opening do not intersect one another.

30. The valve of claim 29 wherein the first valve opening is separated from the second valve opening by an intermediate rib.

31. The valve of claim 28 further comprising:

a third valve opening extending through the valve member, said third valve opening defining a third pathway along the generally convex surface, said third pathway curving along the generally convex surface when viewed from and relative to the perspective along the generally linear axis.

32. In a catheter assembly for use by a patient to control urinary incontinence or retention, said patient having a bladder and a urethra, said bladder having a wall and said urethra having a distal end, said catheter including a catheter body to be disposed at least partially within said urethra of said patient, said catheter body defining a lumen extending from said bladder to said distal end of said urethra and an exterior, and an inflatable balloon connected to said catheter body and disposed at least partially within said bladder so as to retain said catheter body within said urethra and to minimize leakage along said exterior of said catheter body, a collar disposed on said catheter body generally proximate to said distal end of said urethra, said collar for retaining said catheter body and said inflatable balloon in a predetermined position relative to said wall of said bladder and to minimize leakage along said exterior of said catheter body, said collar having a bore and a top surface facing generally proximally toward said patient, the improvement comprising:

a generally concave arcuate surface defined by the top surface of the collar, said generally concave arcuate surface facing towards and the patient to exert tension on the catheter body when the collar is moved to a position wherein said generally concave arcuate surface is contacting the patient.

33. A method of using the catheter assembly of claim 16, the method comprising the steps of:

inserting the catheter body at least partially into the urethra such that the inflatable within the bladder;

(b) inflating the inflatable balloon; and
(c) rotating the collar until the collar is in contact with the surface area proximate the distal end of the urethra and a tension is placed upon the catheter body and the inflated balloon such that the balloon is biased against the inner wall of the bladder and the collar is biased against the surface area surrounding the distal end of the urethra.

* * * * *